United States Patent
Yokoi et al.

(10) Patent No.: US 8,487,271 B2
(45) Date of Patent: Jul. 16, 2013

(54) OPTICAL MICROSCOPE CONFIGURED TO SIMULTANEOUSLY IRRADIATE THE ERASE LIGHT AND THE STIMULATION LIGHT

(75) Inventors: Eiji Yokoi, Tokyo (JP); Yoshinori Iketaki, Oume (JP)

(73) Assignee: Olympus Corporation, Tokyo (JP)

( * ) Notice: Subject to any disclaimer, the term of this patent is extended or adjusted under 35 U.S.C. 154(b) by 650 days.

(21) Appl. No.: 12/553,357

(22) Filed: Sep. 3, 2009

(65) Prior Publication Data

US 2010/0067102 A1    Mar. 18, 2010

(30) Foreign Application Priority Data

Sep. 12, 2008 (JP) ................................. 2008-234738
Mar. 19, 2009 (JP) ................................. 2009-068854

(51) Int. Cl.
*G01N 21/64* (2006.01)
*G01N 21/65* (2006.01)

(52) U.S. Cl.
USPC .......................... 250/458.1; 356/951; 356/952

(58) Field of Classification Search
USPC ......... 356/949, 951, 952; 250/458.1; 359/385
See application file for complete search history.

(56) References Cited

U.S. PATENT DOCUMENTS

| | | | |
|---|---|---|---|
| 5,473,706 A * | 12/1995 | Bacus et al. | 382/133 |
| 5,731,588 A | 3/1998 | Hell et al. | |
| 5,866,911 A | 2/1999 | Baer | |
| 2001/0045529 A1 * | 11/2001 | Iketaki et al. | 250/493.1 |
| 2004/0135079 A1 * | 7/2004 | Moellmann | 250/234 |
| 2005/0264776 A1 * | 12/2005 | Baer | 355/43 |
| 2007/0008615 A1 * | 1/2007 | Miyawaki et al. | 359/385 |
| 2007/0183029 A1 * | 8/2007 | Iketaki | 359/385 |
| 2012/0062722 A1 * | 3/2012 | Sase | 348/79 |

FOREIGN PATENT DOCUMENTS

| | | |
|---|---|---|
| JP | 2002-520612 | 7/2002 |
| WO | WO 00/04352 A1 | 1/2000 |

* cited by examiner

*Primary Examiner* — Mark Consilvio
(74) *Attorney, Agent, or Firm* — Holtz, Holtz, Goodman & Chick, PC

(57) ABSTRACT

The present invention provides an optical microscope capable of suppressing unnecessary response light as a background and detecting desired response light in nonlinear optical response process with a good S/N ratio. The optical microscope for collecting, on a sample 8, stimulation light emitted from a stimulation light source 1 and having a single wavelength or a plurality of different wavelengths, and detecting response light emitted from the sample 8 in nonlinear optical response process, comprises: an erase light source 2 for emitting erase light having a wavelength different from that of the stimulation light and inducing an effect of suppressing secondary response light which appears due to irradiation of the stimulation light on the sample 8, wherein the erase light and the stimulation light are simultaneously irradiated on the sample 8 such that the erase light does not suppress response light emitted from a light-collecting area of the stimulation light but suppresses the secondary response light other than the response light emitted from a light-collecting area of the stimulation light.

21 Claims, 20 Drawing Sheets

OPTICAL MICROSCOPE CONFIGURED TO SIMULTANEOUSLY IRRADIATE THE ERASE LIGHT AND THE STIMULATION LIGHT

CROSS-REFERENCE OF RELATED APPLICATION

The present application claims the priorities of Japanese Patent Application No. 2008-234,738 filed on Sep. 12, 2008 and Japanese Patent Application 2009-068,854 filed on Mar. 19, 2009, which are herein incorporated in the entirety thereof for reference.

BACKGROUND OF THE INVENTION

1. Field of the Invention

The present invention relates to an optical microscope for observing a sample by using nonlinear optical response process.

2. Description of the Related Art

The technique of optical microscopes has a long history, during which various types of optical microscopes have been developed. In recent years, as a result of progress in the peripheral technologies such as laser technology and electronic imaging technology, high-performance optical microscope systems have been developed.

In such a background, high-performance optical microscopes using various spectral processes have been proposed, so that not only a shape of a sample can be analyzed but also a molecule included in the sample can be identified and/or the structure thereof can be analyzed. In recent years, in particular, microscopy detecting response light specific to nonlinear optical response process has been attracting attention since it is capable of easily inducing a nonlinear optical response process with respect to a substance by using pulsed laser having high peak power. Examples of representative nonlinear optical response process include: 1. Raman process; 2. harmonics process (particularly, SHG process); and 3. multiphoton absorption process (particularly, two-photon absorption process). Hereinafter, the respective processes will be briefly explained.

1. Raman Processes

In Raman process, there is Raman spectroscopy in which photoresponse from a biological sample or an industrial material is observed without staining the biological sample or the industrial material to analyze the structure thereof. Raman spectroscopy is expected to be applied to the field of a microscope (see JP2002520612, for example). Raman spectroscopy is based on a type of nonlinear optical effect referred to as Raman effect. When incident light is scattered by a molecule or an atom at high photon flux, a quantum state of the molecule is changed and energy of the entire system is changed. At that time, the changed energy shifts to the scattered photon, whereby, light having a different wavelength from that of the incident light appears. Such a phenomenon is referred to as Raman scattering. As Raman scattering, there are known three types of Raman scattering with the use of monochromatic light, that is, (1) non-resonant Raman scattering, (2) true resonance Raman scattering, and (3) preresonance Raman scattering and one type of Raman scattering with the use of polychromatic light, that is, (4) coherent Raman scattering. Hereinafter, these types of Raman scattering will be further described with reference to FIGS. 24 and 25.

(1) Non-Resonant Raman Scattering

FIG. 24(a) is an energy diagram explaining non-resonant Raman scattering. Non-resonant Raman scattering can be explained by second-order perturbation theory from a viewpoint of an atom and a molecule. Specifically, as shown in FIG. 24(a), non-resonant Raman scattering corresponds to a kind of two-photon process in which a virtual quantum level of S (imaginary) is assumed. In this two-photon excitation process, molecules in a lowest electronic state and a lowest rovibrational level, that is, in the ground state (state $S_0$) are once excited to a virtual quantum level S (imaginary) by, for example, extremely strong laser light and afterwards, de-excited to a high rovibrational level ($V_2$) of the lowest electronic state. As a result, as is apparent from FIG. 24(a), the incident light provides an atom or a molecule with photon energy of ($E_i$-$E_0$), whereby light after non-resonant Raman scattering loses photon energy accordingly and the light is scattered such that the initial wavelength $\lambda_1$ thereof is apparently changed to a longer wavelength of $\lambda_2$. In general, in a two-photon process based on a virtual quantum level including non-resonant Raman scattering, transition probability is extremely small. In order to induce this process, a super short pulsed laser in the order of femtosecond may be required.

(2) True Resonance Raman Scattering

FIG. 24(b) is an energy diagram explaining true resonance Raman scattering. True resonance Raman scattering is a scattering process in which non-resonance Raman scattering satisfies a specific condition that S (imaginary) coincides with the actual first electronically-excited state $S_1$, as shown in FIG. 24(b). This case corresponds to a process in which a molecule of the ground state $S_0$ is excited to the actual first electronically-excited state $S_1$ and then de-excited to a high rovibrational level ($V_2$) of a lowest electronic state. The process, as shown in FIG. 24(b), apparently corresponds to a process in which fluorescence of $\lambda_2$ was emitted after $S_0 \rightarrow S_1$ excitation. Since this true resonance Raman scattering utilizes the actual quantum states scattering probability is extremely high and Raman scattering can be achieved with markedly high light intensity as compared with non-resonant Raman scattering.

(3) Preresonance Raman Scattering

FIG. 24(c) is an energy diagram explaining preresonance Raman scattering. Preresonance Raman scattering has a property intermediate between true resonance Raman scattering and non-resonant Raman scattering. Specifically, this is a case where a level of S (imaginary) exists in the vicinity of the first electronically-excited state $S_1$.

(4) Coherent Raman Scattering

FIG. 25 is a view explaining coherent Raman scattering. FIG. 25(a) is an energy diagram of Coherent Anti-Stokes Raman Scattering (CARS) and FIG. 25(b) is an energy diagram of Coherent Stokes Raman Scattering (CSRS). Coherent Raman scattering is one of the means to study vibration dynamics in a time domain, and various studies thereon have been done in both aspects of experiments and theories.

This coherent Raman scattering is one of the third-order nonlinear optical response processes and generally uses two kinds of laser light (one is $\omega_1$ light and the other is $\omega_2$ light) having different angular frequencies. The laser light which firstly interacts with a molecule $\omega_1$ light and $\omega_2$ light) is also referred to as pump light and Stokes light. When the angular frequency difference between these two types of incident light is identical to the angular frequency $\Omega$ of a vibration mode of sample molecules, a large number of the sample molecules are excited in a resonant vibration mode and with the phases thereof corresponding to each other, i.e. coherently. Since the generated vibration polarization is maintained during the phase relaxation time, the molecules interact with another $\omega_1$ light as probe light during the phase relaxation time, so that coherent Raman scattered light can be taken out as a polarization wave derived from the third nonlinear polarization.

More specifically, by changing delay time between the pump light and probe light, as well as Stokes light and probe light, information about phase relaxation time of molecule vibration can be obtained. In particular, as shown in FIG. 25(a), the Raman scattered light having frequency increased by +Ω is referred to as CARS. In addition, as shown in FIG. 25(b), the Raman scattered light having frequency decreased by −Ω is referred to as CSRS. In the case of CARS, since signal light is detected on the wavelength side shorter than that of excitation light, in particular, CARS is less likely to be affected by the background and the like caused by self fluorescence, whereby signal light can be detected with a good S/N ratio. Therefore, in recent years, CARS has started to be widely applied to spectroscopic microscopes and the like.

As described above, since the CARS process is nonlinear optical response process, signal light is generated only at a specific minute three-dimensional part where laser light, that is, pump light (probe light) and Stokes light are intensely focused. As a result, it is not necessary to introduce a pinhole as in a confocal microscope, whereby three-dimensional space resolution performance, which is excellent in essence, can be realized by introducing a CARS process into a scanning laser microscope. Besides, since a biological sample can be observed without being stained, the marketing prospect thereof is very promising.

2. Harmonics Process

The phenomenon attributed to the harmonics process is often observed and widely applied in the field of laser optics. For example, when laser light having a certain wavelength is made incident on an optical medium having a dielectric structure in which wavelengths are spatially in order, harmonic wave is generated from this optical medium. Specifically, a dielectric body is subjected to forced oscillation in its oscillating electric field by intense laser light and generates as a second-order wave an oscillating electric field having distortion that is not proportional to the amplitude of the oscillating electric field (a nonlinear optical effect). As a result, coherent light having a component multiplied by an integer with respect to the oscillation frequency of the incident laser light is generated. Especially, in a case where a crystal having an appropriate periodic nature is used, an extremely intense, frequency-doubled harmonic wave is generated. Therefore, it is possible to convert incident light into laser light having an arbitrary wavelength by adjusting the type of crystals and an incident angle.

This phenomenon is also applied to microscopy. For example, in a case where an observation sample has a periodic structure, when it is irradiated by coherent laser light, the sample generates a second-harmonic wave having an oscillation frequency twice as much as that of the illumination light due to its periodic structure. In other words, light having a halved wavelength occurs. By catching this second-harmonic light, a microscopic image can be obtained. Accordingly, the harmonic process is attracting attention in recent years since it allows a sample to be observed without being stained as in Raman process. The harmonic process basically utilizes a nonlinear optical effect as in Raman process.

3. Multiphoton Absorption Processes

A molecule usually has an electronic state determined by a bonding state of a valence electron of a constituent atom and has a quantum-mechanically discrete energy level. Further, an oscillation state in which bond distances between atomic nucleuses oscillate and a state such as rotation movement of the entire molecule are overlapped. In particular, when a molecule is illumination-excited from the lowest state, that is, the ground state to the next excited electronic state (the first electronically-excited state, see FIG. 24), intense fluorescence is generated from the first electronically-excited state. A typical fluorescent microscope captures this fluorescence for imaging. In this case, it is necessary to use illumination light having higher photon energy than an energy gap between the ground state and the first electronically-excited state.

On the other hand, a laser source emitting pulsed light having extremely high energy peak power is commercially available recently and thus a fluorescent microscopy (a multiphoton microscope) utilizing a multiphoton absorption process is available. In this multiphoton absorption process based on the nonlinear optical effect as in the harmonic process, when a molecule is excited from the ground state to the first electronically-excited state, the molecule is made to absorb a plurality of photons at the same time to generate fluorescence. What is characteristic of this process is that it requires photon energy of the illumination light which is much less than the above-mentioned energy gap. For example, a molecule simultaneously absorbs two photons in a two-photon process so that photon energy, which is a half of the above-mentioned energy gap, suffices.

This means that, with regard to wavelength, illumination light having wavelength twice as long as that of conventional illumination light suffices. Therefore, it is possible to normally use visible light as illumination light and, in the case of a two-photon process, use excitation light of near-infrared, whereby compact and stable semiconductor laser and fiber laser can be utilized. Further, since the responsive amount of fluorescence is proportional to square of irradiation intensity, a fluorescence responsive region is limited in a very small region in a three-dimensional space. In a case where light is focused, the responsive region in the optical axis direction becomes very small, whereby three-dimensional space resolution can be obtained, which is impossible in conventional fluorescent microscopy.

SUMMARY OF THE INVENTION

As described above, various microscopes using nonlinear optical response processes can provide a nonconventional superior function. However, problems associated with the nonlinear optical response process have been identified and the measures are demanded. Especially, microscopy utilizing various Raman processes (Raman microscope), which is very promising since a biological sample can be observed without being stained, has very serious problems as described below.

For example, in the case of microscopes utilizing nonresonant Raman scattering described in the item (1) above and coherent Raman scattering described in the item (4) above, there arises a problem that a photoresponse cross-section, that is, a Raman scattering cross-section is extremely small. Specifically, in the case of a typical fluorescent microscope, a photoresponse cross-section with respect to excitation light, that is, an absorption cross-section, is about $10^{-16}$ $cm^2$. In contrast, a Raman scattering cross-section is much smaller than this and about $10^{-21}$ $cm^2$. Therefore, there is a problem that extremely little amount of Raman scattered light (signal light) is detected in a typical light source, that is, in a laser light source.

The problem described above is generally addressed by using a high-power femtosecond laser based on a titanium sapphire laser, which is expensive and difficult to operate, or by prolonging measurement time to increase the signal amount. However, in the case of using a high-power femtosecond laser, a sample may suffer damage, which becomes a problem if a living biological sample is observed. In addition, in the case of prolonging measurement time, an S/N ratio is degraded and time for capturing one picture increases significantly. Therefore, at present the measurement conditions are set in consideration of somehow trading-off these conditions.

Since extremely intense excitation light (hereinafter, referred to as stimulation light) is irradiated in order to induce Raman process, there arises a possibility that fluorescent emission may occur from, for example, a solvent surrounding a biological sample, a cover glass or the like other than the object sample to be observed. The causes for occurrence of such a situation include that luminescent impurity molecules, which are not necessary for observation but exist as contaminants in a sample or on a glass, are fluorescently excited in the multiphoton absorption process. In this case, light having wavelength components other than the response light to be detected with respect to the stimulation light will be detected in a wavelength region. In this situation, in terms of detection space, although photoresponse only from the light-collecting area of the stimulation light is to be detected, unnecessary fluorescence signals and the like from, for example, a cover glass boundary will also be detected.

As a result, a microscope adopting a laser scanning method, in which stimulation light is collected on a sample and the sample is spatially and relatively scanned with respect to the light-collecting point, encounters a serious problem that a week Raman signal is buried in background signals. This is due to increase in unnecessary secondary response light, i.e. background light, which is inevitably caused in a wavelength region and a spatial region by a nonlinear optical response process of Raman process.

On the other hand, in the case of a microscope utilizing true resonance Raman scattering as described in the item (2) above or pre-resonance Raman scattering as described in the item (3) above, the Raman scattering cross-section is relatively close to the absorption cross-section of electronic transition and up to $10^{-17}$ cm$^2$, which is the same degree of cross-section as that of a normal fluorescent microscope. Accordingly, in such a microscope as described above, there are merits that a measurement time can be shortened and degree of freedom in use of a light source is relatively high.

However, in the case of the aforementioned microscope, background signals are so increased that an S/N ratio is extremely low. In other words, in the case of such a microscope as described above, the wavelength of excitation light is closer to the wavelength of the resonance level of $S_0 \rightarrow S_1$ in which the electronic transition is possible. In this case, when the wavelength of excitation light reaches a sidelobe on the longer wavelength side of $S_0 \rightarrow S_1$ absorption band, $S_0 \rightarrow S_1$ absorption begins and fluorescence emission from a $S_1$ state simultaneously occurs.

Since Raman signal light generally appears on the longer wavelength side than that of illumination light, especially in the case that resonance Raman scattering is used, the wavelength range of Raman signal light overlaps with that of fluorescence from the $S_1$ state and even a relatively intense Raman signal will be eclipsed by fluorescence. Therefore, substantially only a part of molecules having a relatively low fluorescence yield can be an observation object. That is, the fluorescence generated by the observation object molecule itself functions as background light in the wavelength region.

A similar problem also occurs in, for example, a two-photon microscope utilizing a multiphoton absorption process. In a two-photon microscope, it may be assumed, theoretically, that the microscope is capable of analyzing a deep part of a sample because stimulation light has the wavelength of near-infrared light, is transparent with respect to a biological sample and has three-dimensional space resolution. However, in fact, as shown in FIG. 26, in a case where a sample 101 is a scattering substance, intense scattering occurs at an interface 102 as an optical interface between a cover glass which is an optical interface and the sample 101 and simultaneously second fluorescence is generated in the vicinity of the above-mentioned interface regions which is outside of a light-focusing point of stimulation light. Further, in the case where the light-collecting point of the stimulation light by a microscope objective lens 103 is positioned in a deep part away from the above-mentioned interface 102, total light amount of the stimulation light arriving as a result of scattering is decreased and fluorescence intensity of the response light to be detected is decreased. Besides, since the fluorescence amount of the response light is proportional to square of irradiation intensity, an influence thereof is rendered conspicuous. As a result, background light due to secondary response light from the vicinity of the interface region is made relatively intense, whereby it is substantially impossible to observe a deep part of the substance. Such a problem also occurs in a microscope utilizing the harmonics process.

It is, therefore, an object of the present invention which has been made in view of the above-mentioned problems is to provide an optical microscope capable of detecting desired response light according to a nonlinear optical response process with a good S/N ratio by suppressing unnecessary response light which would function as a background.

In a first aspect of the present invention to achieve the above-mentioned object, an optical microscope for collecting, on a sample, stimulation light emitted from a stimulation light source and having a single wavelength or a plurality of different wavelengths, and detecting response light emitted from the sample in nonlinear optical response process, comprises: an erase light source for emitting erase light having a wavelength different from that of the stimulation light and inducing an effect of suppressing secondary response light which appears due to irradiation of the stimulation light on the sample, wherein the erase light and the stimulation light are simultaneously irradiated on the sample such that the erase light does not suppress response light emitted from a light-collecting area of the stimulation light but suppresses the secondary response light other than the response light emitted from a light-collecting area of the stimulation light.

In a second aspect of the present invention, the optical microscope of the first aspect is characterized in that the erase light source emits, as the erase lights light having such a wavelength as to suppress fluorescence of the secondary response light.

In a third aspect of the present invention, the optical microscope of the second aspect, further comprises an optical separation element for optically separating the stimulation light and the erase light to be irradiated on the sample from the response light from the sample.

In a fourth aspect of the present invention, the optical microscope of the third aspect, is characterized in that the optical microscope is arranged to detect scattered light as the response light.

In a fifth aspect of the present invention, the optical microscope of the fourth aspect is characterized in that the optical microscope is arranged to detect light which has been stimulated and scattered in Raman process, as the scattered light.

In a sixth aspect of the present invention, the optical microscope of the fourth aspect is characterized in that the optical microscope is arranged to detect light which has been stimulated and scattered in resonance Raman process, as the scattered light.

In a seventh aspect of the present invention, the optical microscope of any of the fourth to sixth aspects is characterized in that the optical microscope is arranged to suppress the secondary response light in a double resonance absorption process or a stimulated emission process.

In an eighth aspect of the present invention, the optical microscope of the fifth or sixth aspect is characterized in that the optical microscope is arranged to detect, as the response light, response light from a sample stained by a fluorescent probe.

In a ninth aspect of the present invention, the optical microscope of the eighth aspect is characterized in that the optical microscope is arranged to be capable of switching between a scattered light detection mode in which the stimulation light and the erase light are simultaneously irradiated on the sample to detect the scattered light and a fluorescence detection mode in which only the stimulation light is irradiated on the sample to detect fluorescence by the fluorescent probe.

In a tenth aspect of the present invention, the optical microscope of the third aspect is characterized in that the optical microscope is arranged to detect, as the response light, fluorescence induced by a multiphoton absorption process.

In an eleventh aspect of the present invention, the optical microscope of the tenth aspect is characterized in that the optical microscope is arranged to detect, as the response light, fluorescence from a sample stained by a fluorescent probe.

In a twelfth aspect of the present invention, the optical microscope of any of the first to eleventh aspects further comprises an adjusting means for adjusting any one of a light-collecting position, a light-collecting size and light-collecting intensity of the stimulation light or the erase light.

In a thirteenth aspect of the present invention, the optical microscope of the twelfth aspect is characterized in that the adjusting means comprises a wavefront modulation element for modulating wavefront of the erase light and decreasing peak power at a light-collecting position.

In a fourteenth aspect of the present invention, the optical microscope of the thirteenth aspect is characterized in that the adjusting means makes a light-collecting position of the stimulation light different from a light-collecting position of the erase light.

In a fifteenth aspect of the present invention, the optical microscope of any of the first to fourteenth aspects is characterized in that the erase light source emits near-infrared light as the erase light.

In a sixteenth aspect of the present invention, the optical microscope of any of the first to fifteenth aspects is characterized in that the stimulation light source and the erase light source are pulsed light sources respectively, the stimulation light source emits stimulation light having a pulse width of not more than 10 picoseconds and the erase light source emits erase light having a pulse width longer than the pulse width of the stimulation light.

In a seventeenth aspect of the present invention, the optical microscope of any of the first to sixteenth aspects is characterized in that the stimulation light source or the erase light source includes any one of a titanium sapphire laser, a Nd:YAG laser, a fiber laser, a semiconductor laser and a super-continuum light source.

In an eighteenth aspect of the present invention, the optical microscope of any of the first to seventeenth aspects, comprises: a secondary light detecting means for detecting the secondary response light generated at a surface of the sample; and an erase light intensity adjusting means for adjusting intensity of the erase light emitted from the erase light source based on output of the secondary light detecting means.

In a nineteenth aspect of the present invention, the optical microscope of any of the first to seventeenth aspects, comprises: a response light detecting means for detecting the response light emitted from the sample; an image processing means for generating an image signal based on output of the response light detecting means; and an intensity setting means for setting intensity of the erase light emitted from the erase light source, based on an image signal obtained from the image processing means.

In a twelfth aspect of the present invention, the optical microscope of the nineteenth aspect is characterized in that: the intensity setting means generates histogram showing intensity distribution of the response light, based on an image signal obtained from the image processing means, and sets optimum intensity of the erase light based on a change in the histogram in relation to intensity change of the erase light emitted from the erase light source.

In a twenty-first aspect of the present invention, the optical microscope of any of the first to twentieth aspects is characterized in that intensity of the erase light irradiated on the sample is not more than the predetermined highest intensity under which a second emission phenomenon due to irradiation of the erase light does not occur.

In a twenty-second aspect of the present invention, the optical microscope of any one of the first to twenty-first aspects, comprises an erase light irradiation means for irradiating the sample with the erase light emitted from the erase light source, which is erase light having two-dimensional sheet-like intensity distribution.

According to the present invention, stimulation light and erase light having a wavelength different from that of the stimulation light simultaneously are irradiated on the sample such that response light emitted from a light-collecting area of the stimulation light is not suppressed but secondary response light other than the response light is suppressed. As a result, it is possible to detect desired response light according to a nonlinear optical response process, with a good S/N ratio, by suppressing unnecessary response lights which is to be a background, from occurring.

DESCRIPTION OF THE PREFERRED EMBODIMENTS

Summary of the Present Invention

At first, the outline of the present invention will be described before the embodiments of the present invention are described.

Figure 1:
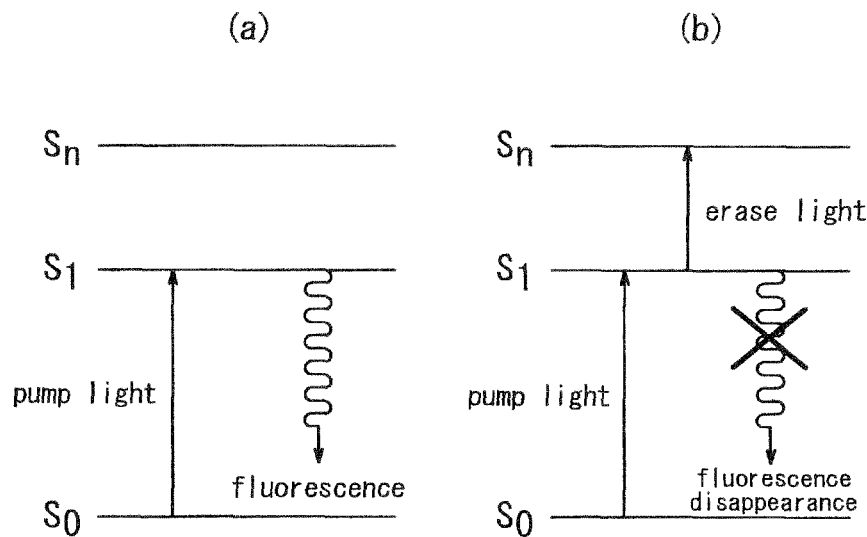
FIG. 1 is a view for explaining the principle of two-color fluorescence Dip spectroscopy.

Nowadays, super-resolution microscopy technique has been developed in the field of a fluorescent microscope. This technique employs a kind of spectroscopic process of two wavelengths, that is, two-color fluorescence Dip spectroscopy. The principle of this two-color fluorescence Dip spectroscopy will be explained with reference to FIGS. 1(a) and 1(b). Firstly, as shown in FIG. 1(a), a molecule is excited to a $S_1$ state by pump light and next, as shown in FIG. 1(b) the molecule is further excited from the $S_1$ state to a $S_n$ state by irradiation of erase light (double resonance absorption process).

Figure 2:
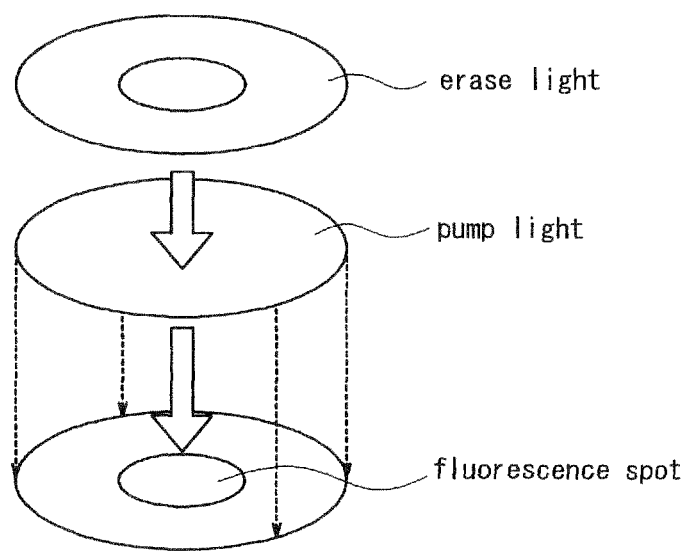
FIG. 2 is a view for explaining the principle of super-resolution microscopy.

Generally, a molecule in a highly-excited state $S_n$ does not emit fluorescence by a fast non-radiation process. Therefore, in a region where two types of light overlap, a molecule is excited to $S_n$ and fluorescence from $S_1$ disappears (fluorescence suppression effect). In addition, when erase light overlaps with a fluorescence emission band, an induced emission process also occurs, contributing to the fluorescence suppression effect. Accordingly, for example, as shown in FIG. 2, when erase light is shaped into a doughnut-like configuration and irradiated on the sample in a manner of light-collecting irradiation such that a part of the erase light spatially overlaps with pump light, a fluorescence spot shrinks to a size of not more than a diffraction limit determined by a numerical aperture and a wavelength of a microscope objective lens (not illustrated), due to the fluorescence suppression effect. Super-resolution microscopy is achieved when a sample position is scanned in this state.

What is important here is that it is possible to completely suppress the fluorescence by simultaneously irradiating a sample with erase light having a band on the longer wavelength side away from the absorption band where $S_0 \rightarrow S_1$ absorption does not occur. Specifically, light, having a band on the longer wavelength side where $S_0 \rightarrow S_1$ absorption does not occur, functions as erase light. In general, such a wavelength band as described above spreads from a visible light region to a near-infrared region. Further, in recent years, there has been developed an advanced technology using a two-photon process, as well, in exciting a molecule with pump light (see JP2001-272343, for example).

By utilizing the fluorescence suppression effect by this erase light, it is possible to remove secondary background light which occurs in various nonlinear optical response processes. For example, in a case this effect is applied to microscopy utilizing the resonance Raman process, it is possible to measure only a strong resonance Raman signal without being disturbed by a secondary fluorescence signal. In this case, two types of color laser sources are prepared as a light source of a Raman microscope. One of the two color laser sources is a resonance Raman laser source which oscillates light having a wavelength capable of inducing resonance Raman with respect to a molecule as an observation object. The other is a laser source which oscillates erase light to induce the fluorescence suppression effect. The wavelength of the erase light is preferably in a near-infrared region on the longer wavelength side sufficiently away from a wavelength of a resonance Raman signal. There are available various types of laser sources having a wavelength band of this range.

In an embodiment of the present invention, laser light from a resonance Raman laser source (Raman process-inducing stimulation light) is irradiated, together with erase light from an erase light source, on a sample, to utilize the aforementioned fluorescence suppression effect of the erase light. In this way, fluorescence due to irradiation of Raman process-inducing stimulation light can be completely suppressed by erase light. As a result, it is possible to remove fluorescence, which would be a background otherwise, and take out only the resonance Raman signal for detection.

In addition, this principle can be effectively applied to a coherent Raman microscope using coherent Raman scattering. In a coherent Raman microscope, pump light and probe light are generally prepared and a light source is adjusted such that difference in frequency between these two types of light coincides with the natural frequency of the chemical base of an observation object. It is noted that the pump light and the probe light are selected such that each of the lights has a wavelength where $S_0 \rightarrow S_1$ absorption does not occur.

By applying the present invention to such a coherent Raman microscope so that an observation area thereof is simultaneously irradiated with erase light in addition to pump light and probe light, to suppress fluorescence similarly, it is possible to bring the wavelengths of pump light and probe light closer to a wavelength where $S_0 \rightarrow S_1$ absorption occurs to thereby induce resonance Raman process. The coherent Raman process utilizes a tertiary non-linear optical effect employing two-color light sources. In other words, assuming that pump light intensity is P1 and probe light intensity is P2, obtained Raman scattering signal intensity, that is, signal intensity I is given in the following expression (1).

[Expression 1]

$$I \propto P_1^2 P_2 \qquad (1)$$

As is apparent from the expression (1), intensity of a Raman scattering signal is in proportion to probe light intensity and the square of pump light intensity at a light-collecting surface of a sample due to a non-linear effect. Therefore, when a Raman scattering cross-section is increased in resonance Raman process, signal intensity is increased in the order of power of three, whereby remarkably intense Raman signal, as compared with conventional coherent Raman microscopy, can be obtained by suppressing unnecessary fluorescence by applying the present invention. Further, measurement time and a S/N ratio can also be significantly improved.

Needless to say, the present invention can be applied to an ordinary microscopy utilizing non-resonance Raman scattering process. In this case, there is expected a greater effect of removing fluorescence light having a different wavelength from that of Raman light as response light in a spectral range. In addition, since the cross-section with respect to the fluorescence suppression by erase light is larger than the cross-section in Raman process, unnecessary fluorescence which occurs outside of a light-collecting point of Raman process-inducing stimulation light can be spatially suppressed by irradiation of erase light.

In addition, the present invention can be applied to a two-photon microscope to remove background light by utilizing the fluorescence suppression effect of erase light. In this case, erase light is collected, for example, on an interface between a sample and a cover glass. By doing this, as mentioned above, it is possible to suppress, by erase light, secondary response light occurring mainly at an interface between a sample and a cover glass, that is, unnecessary fluorescence light which is not a detection object. Besides, the fluorescence suppression effect by erase light can be ignored with respect to fluorescence occurring at a light-collecting point of stimulation light in the sample, which light-collecting point is away from the interface, that is, with respect to response light, because a light-collecting point of stimulation light is sufficiently away from a light-collecting point of erase light and only week erase light arrives at the light-collecting point of stimulation light. As a result, it is possible to make intensity of response light relatively strong, as compared with background light, whereby a fluorescence picture of a deep part of the sample can be obtained with a good S/N ratio.

In addition, the present invention can be applied to a microscope utilizing the harmonics process to produce a similar improvement effect. In this case, there is obtained an effect that fluorescence light occurring at another medium having a different wavelength from the fluorescence wavelength of response light is removed in a spectral range and at the same time fluorescence emitted from a spatial region different from a light-collecting point of stimulation light is spatially separated and removed.

Next, the embodiments of a microscope according to the present invention will be described.

First Embodiment

A microscope according to the first embodiment of the present invention visualizes a biological molecule by using resonance Raman scattering. The Biological sample includes, for example, nucleobase such as tryptophan, tyrosine, phenylalanine and adenine. Such nucleobase, which is an important molecule to analyze living structure and activity thereof, includes a benzene ring and a nitrogen base and has a $S_0 \rightarrow S_1$ absorption band by extremely strong electronic transition in a wavelength band around 260 nm. Thus, if these molecules are exited by fourth-harmonic wave of Nd:YAG laser light (wavelength 266 nm) as Raman process-inducing stimulation light, Raman band can be made to appear in a wavelength band of 290 nm to 400 nm.

However, the above-mentioned molecules have a strong fluorescence band around the wavelength of 360 nm. Therefore, in conventional resonance Raman scattering microscopy using only Raman process-inducing stimulation light, a fluorescence band becomes a background and a good S/N ratio will not be obtained in a series of Raman bands.

Therefore, in the present embodiment, upon noticing that tryptophan has a double resonance absorption band by $S_1 \rightarrow S_1$ in a wavelength region from 600 nm to a near-infrared region, a titanium sapphire laser capable of emitting intense laser light in this wavelength region, for example, is used as an erase light source, to irradiate a biological sample with the erase light emitted from the erase light source, simultaneous with Raman process-inducing stimulation light. In this way, fluorescence in a wavelength band from 290 nm to 400 nm, in which Raman band appears, can be suppressed, so that high-purity of Raman band components can be obtained and a resonance Raman signal can be detected with a high S/N ratio.

Figure 3:
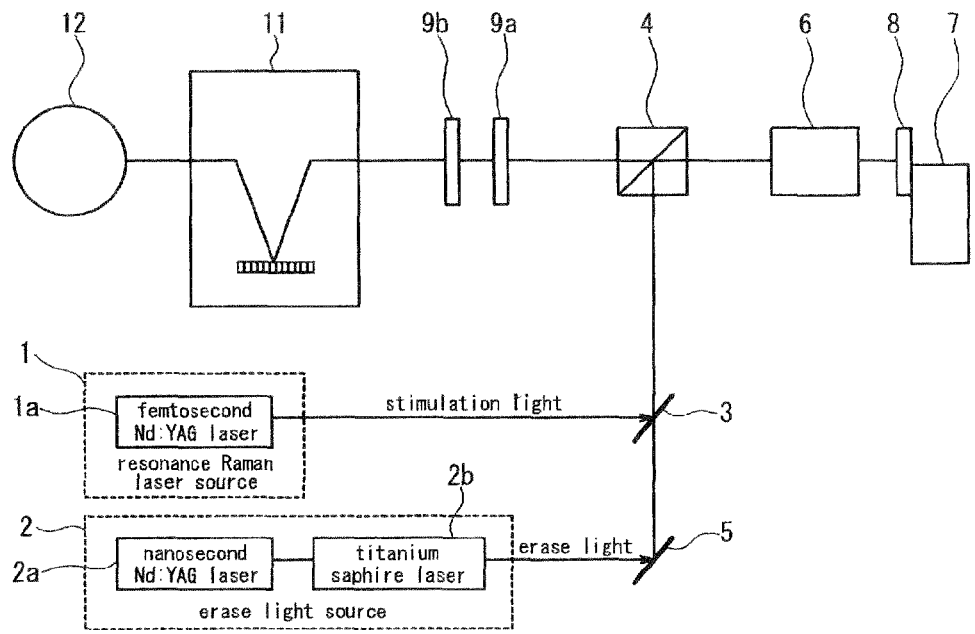
FIG. 3 is a schematic block diagram of a main part of a scanning resonance Raman laser microscope according to a first embodiment of the present invention.

FIG. 3 is a schematic block diagram of a main part of a scanning resonance Raman laser microscope according to the present embodiment. This scanning resonance Raman laser microscope has a resonance Raman laser source 1 which is a stimulation light source and erase light source 2. The resonance Raman laser source 1 has, for example, a femtosecond Nd:YAG laser 1a of mode lock type, which outputs pulsed light having a pulse width of not more than 10 picoseconds and uses a fourth-harmonic wave (wavelength 266 nm) as Raman process-inducing stimulation light (Raman process-inducing stimulation light. The pulsed laser light emitted from this femtosecond Nd:YAG laser 1a has high peak power so that a Raman signal can be sufficiently generated.

The erase light source 2 has, for example, a nanosecond Nd:YAG laser 2a and a titanium sapphire laser 2b which uses a second-harmonic wave of the laser light emitted from the nanosecond Nd:YAG laser 2a as excitation light. The erase light source 2 uses the pulsed laser light emitted from this titanium sapphire laser 2b and having a longer nanosecond pulse width than that of Raman process-inducing stimulation light. The erase light source 2 of this configuration can arbitrarily vary a wavelength of the output light thereof on the wavelength side longer than 700 nm. Since a fluorescence process of a molecule in a near-infrared region is generally induced by a two-photon absorption process, in the present embodiment, in order that a two-photon absorption process does not occur in the near-infrared region, erase light emitted from the erase light source 2 is made to have normal peak power having around a thousandth of intensity in which a two-photon absorption process occurs.

The Raman process-inducing stimulation light emitted from the resonance Raman laser source 1 is reflected by a dichroic mirror 3 and incident on a polarization beam splitter 4 which is an optical separation element. The erase light emitted from the erase light source 2 is reflected by a reflecting mirror 5 and thereafter transmitted through the dichroic mirror 3, thereby coaxially combined with the Raman process-inducing stimulation light emitted from the resonance Raman laser source 1 to be incident on the polarization beam splitter 4.

The combined light of the Raman process-inducing stimulation light and the erase light, which is incident on the polarization beam splitter 4, is reflected by the polarization beam splitter 4 and then collected on a biological sample 8 supported on a sample stage 7 via a microscope objective lens 6. As a result, only Raman scattered light is emitted from the biological sample 8 due to a fluorescence suppression effect by the erase light.

Raman scattered light emitted from the biological sample 8 is passed through the microscope objective lens 6, incident on the polarization beam splitter 4 and transmitted through the polarization beam splitter 4 so that Raman process-inducing stimulation light and erase light are optically separated. The Raman scattered light separated by the polarization beam splitter 4 is passed through a notch filter 9a for cutting Raman process-inducing stimulation light, a high pass filter 9b for cutting erase light and a spectroscope 11 and thereafter received by a photomultiplier tube 12, by which Raman spectrum is measured. The combined light-collecting on the biological sample 8 is two-dimensionally scanned by driving by a computer a sample stage 7 and/or a scanning optical system control not illustrated, whereby a two-dimensional Raman signal is measured.

In this way, in the present embodiment, since the Raman process-inducing stimulation light and the erase light for suppressing fluorescence in the wavelength region where Raman band appears are simultaneously irradiated on the biological sample 8, fluorescence by irradiation of the Raman process-inducing stimulation light can be completely suppressed by the erase light. As a result, fluorescence which could become a background can be removed and only a resonance Raman signal can be detected with a high S/N ratio. It is noted that in FIG. 3, since the wavelength bands of the Raman process-inducing stimulation light and the erase light, which are respectively cut by the notch filter 9a and the high pass filter 9b, are significantly different from the wavelength band in which Raman scattered light appears, reduction in the amount of Raman scattered light to be detect can be ignored. In addition, $S_1 \rightarrow S_1$ in molecules included in the biological sample 8 generally spreads widely in a near-infrared region, self fluorescence from a very small amount of molecule other than test substance can be also suppressed by irradiation of the erase light, so that background signals in an observation region can be further surely removed.

Second Embodiment

Environmentally responsive fluoroprobe of a biological sample is observed with a microscope according to a second embodiment of the present invention, by utilizing coherent Raman scattering. In a coherent Raman microscope, staining a biological sample is not generally required because resonance oscillation of a molecule is converted to signals. However, when environmentally responsive fluoroprobe is observed with a conventional coherent Raman microscope, a two-photon absorption process and the like may follow and there is a possibility that a Raman signal is buried among fluorescence signals and cannot be detected.

By the way, when an environmentally responsive fluoroprobe takes in or absorbs a particular molecule, atom or ion, it greatly increases a fluorescence yield and emits intense fluorescence. Further, a fluorescence yield greatly varies depending on ambient temperature and pressure so that the environmentally responsive fluoroprobe is either fluorescent or non-fluorescent. Thus, once the environmentally responsive fluoroprobe is changed to be fluorescent in response to the environment, the presence thereof can be observed by normal fluorescent microscopy. However, in this case, behavior and presence of the probe molecule which is non-fluorescent before an environmental response cannot be observed.

A coherent Raman microscope is cited as a means of observing such a non-fluorescent probe molecule. However, even such a supposed-to-be non-fluorescent probe molecule emits some fluorescence of background signals (i.e. the fluorescence yield thereof is not absolutely zero), thereby competing with a Raman signal. Therefore, in a conventional coherent Raman microscope, a non-fluorescent probe molecule before an environmental response may not be observed with a good S/N ratio.

Thus, in the present embodiment, an erase light source is introduced into a Coherent Anti-Stokes Raman Scattering (CARS) microscope so that fluorescence signals which could become background signals are similarly suppressed by means of erase light from the erase light source. A case will be explained hereinbelow, as an example, where fluorescence calcium indicator Rhod2, which becomes fluorescent upon intake of calcium ion therein, is observed as an environmentally responsive fluoroprobe. It is known that Rhod2 has intense $S_1$ absorption with respect to light having a wavelength around 550 nm and emits intense fluorescence having a wavelength around 580 nm after intake of calcium ion.

Figure 4:
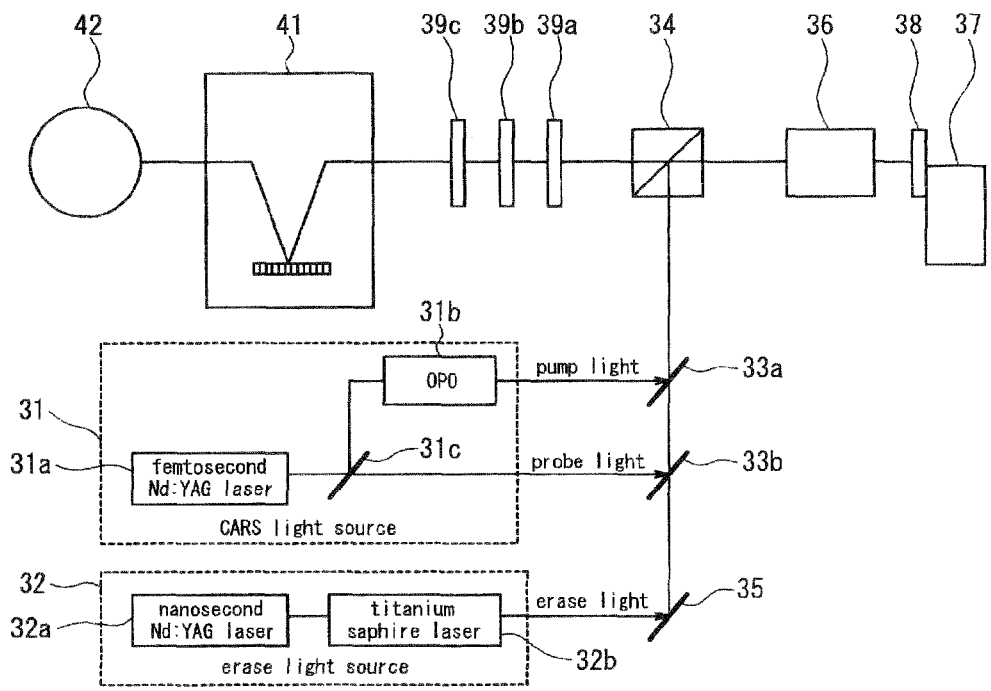
FIG. 4 is a schematic block diagram of a main part of a CARS microscope according to a second embodiment of the present invention.

FIG. 4 is a schematic block diagram of a main part of a CARS microscope according to the present embodiment. This CARS microscope has a CARS light source 31 which is a stimulation light source and an erase light source 32. The CARS light source 31 has, for example, a femtosecond Nd:YAG laser 31a of mode lock type, which outputs pulsed light having a pulse width of not more than 10 picoseconds and an Optical Parametric Oscillator (OPO) 31b which is a nonlinear wavelength conversion optical element. In the CARS light source 31, the pulsed laser light having a second-harmonic wave (wavelength 532 nm) of laser light emitted from the femtosecond Nd:YAG laser 31a is used as probe light, and a part of this probe light is branched by a half mirror 31c, whereby the branched light is incident on the OPO 31b as excitation light and pulsed laser light emitted from the OPO 31b is used as pump light. The OPO 31b oscillates pump light on the wavelength side longer than 532 nm in a wavelength variable manner. In the present embodiment, a wavelength of the pump light emitted from this OPO 31b is 650 nm and frequency difference between the pump light and the probe light is 2900 Kevin which corresponds to a natural frequency of the CH basis included in Rhod2. Therefore, in the present embodiment, the pump light and the probe light correspond to stimulation light.

An erase light source 32, like the erase light source 2 as shown in FIG. 3, has a nanosecond Nd:YAG laser 32a and a titanium sapphire laser 32b which uses a second-harmonic wave of laser light emitted from the nanosecond Nd:YAG laser 32a as excitation light. The erase light source 32 uses, as erase light, pulsed laser light emitted from the titanium sapphire laser 32b and having a nanosecond pulse width longer than that of the pump light and the probe light. In the present embodiment, the erase light having a wavelength of 730 nm is output from this erase light source 32.

The pump light emitted from the CARS light source 31 is reflected by a dichroic mirror 33a and the thus reflected pump light is incident on a polarization beam splitter 34 which is an optical separation element. The probe light emitted from the CARS light source 31 is reflected by a dichroic mirror 33b and the reflected probe light is transmitted through the dichroic mirror 33a, so that the light is then coaxially combined with the pump light to be incident on the polarization beam splitter 34. In addition, the erase light emitted from the erase light source 32 is reflected by a reflecting mirror 35 and the reflected erase light is transmitted through the dichroic mirror 33b and the dichroic mirror 33a, whereby the light is coaxially combined with the probe light and the pump light to be incident on the polarization beam splitter 34.

The pump light, the probe light and the erase light, which are coaxially combined to be incident on the polarization beam splitter 34, are reflected by the polarization beam splitter 34 and thereafter the thus-reflected light is passed through a microscope objective lens 36 and collected on a biological sample 38 supported on a sample stage 37.

Response light from the biological sample 38 is incident on the polarization beam splitter 34 via the microscope objective lens 36, and transmitted through the polarization beam splitter 34 to be optically separated into the pump light, the probe light and the erase light. Response light separated by the polarization beam splitter 34 is passed through a pump light cut filter 39a, a probe light cut filter 39b, an erase light cut filter 39e and a spectroscope 41 and thereafter received by a photomultiplier tube 42, by which Raman spectrum is measured. As is the case of the first embodiment, the combined light-collecting on the biological sample 38 is two-dimensionally scanned by driving by a controller the sample stage 37 and/or a scanning optical system not illustrated, whereby a two-dimensional Raman signal is measured.

According to the present embodiment, since the biological sample 38 is simultaneously irradiated with the erase light in addition to the pump light and the probe light in observing Raman spectrum of the biological sample 38 in the CARS microscopy, the fluorescence of Rhod2 of a wavelength region which could become a background can be suppressed by the erase light. Therefore, a S/N ratio of a Raman signal of Rhod2 can be increased and thus Raman spectrum of Rhod2 can be observed with a high degree of accuracy.

In addition, in the present embodiment, it is possible to measure a Raman signal in whatever environment Rhod2 exists because a sample is irradiated with erase light at the same time. Therefore, for example, by measuring a particular part of Rhod2 by Raman scattering in the CARS microscopy with simultaneous irradiation of erase light (a scattered light detection mode) and detecting fluorescence due to Rhod2 by at any time switching to normal fluorescent microscopy therefrom (a fluorescence detection mode) to confirm reaction situation with calcium, it is possible to observe the moment when probe molecules are reacted with calcium. Switching to a fluorescence detection mode in a conventional fluorescent microscopy can be easily attained, for example in the FIG. 4 structure, by stopping irradiation of the erase light, irradiating the biological sample 38 with the pump light and the probe light and replacing the erase light cut filter 39c with a filter for transmitting fluorescence. Further, even if a fluorescence yield dropped due to discoloration after reaction, probe molecules can be traced according to the CARS microscopy by simultaneous irradiation of the erase light. Further, since resonance Raman process is used in the present embodiment, the amount of a Raman signal is increased and the measurement time can be shortened, as compared with a normal CARS microscopy.

In FIG. 4, environmentally responsive fluoroprobe has been described by using, as an example, Rhod2 which is a probe for detecting calcium. However, other environmentally responsive fluoroprobe can also be observed in a similar manner. For example, benzofurazan shows fluorescence in hydrophobic environment and the fluorescence yield thereof decreases in hydrophilic environment. In this case, the probe can be made visible by tracking the probe in hydrophilic environment. Further, since the probe molecule is observed while its fluorescence is being suppressed, even in fluorophores which cannot be observed in conventional Raman microscopy, an oscillation spectrum can be measured by suppressing fluorescence. Accordingly, it is possible to observe fluorescence protein of high interest in the field of biology such as GFP, YFP, RFP and CFP as well as Dorohpa and Kaede which can be optically modified.

In FIG. 4, the CARS light source 31 is not limited to a femtosecond Nd:YAG laser 31a of mode lock type but may comprise a femtosecond titanium sapphire laser or a short pulsed laser system combining a semiconductor laser with a fiber amplifier. Further, the CARS light source 31 and the erase light source 32 can use a super-continuum light source which outputs white laser light by introducing laser light from a femtosecond titanium sapphire laser to a photonic crystal fiber and be configured such a manner that the white light from this super-continuum light source is incident on a wavelength dispersion element such as an optical filter or a spectroscope to take out excitation light and erase light having a desired wavelength.

Third Embodiment

Figure 5:
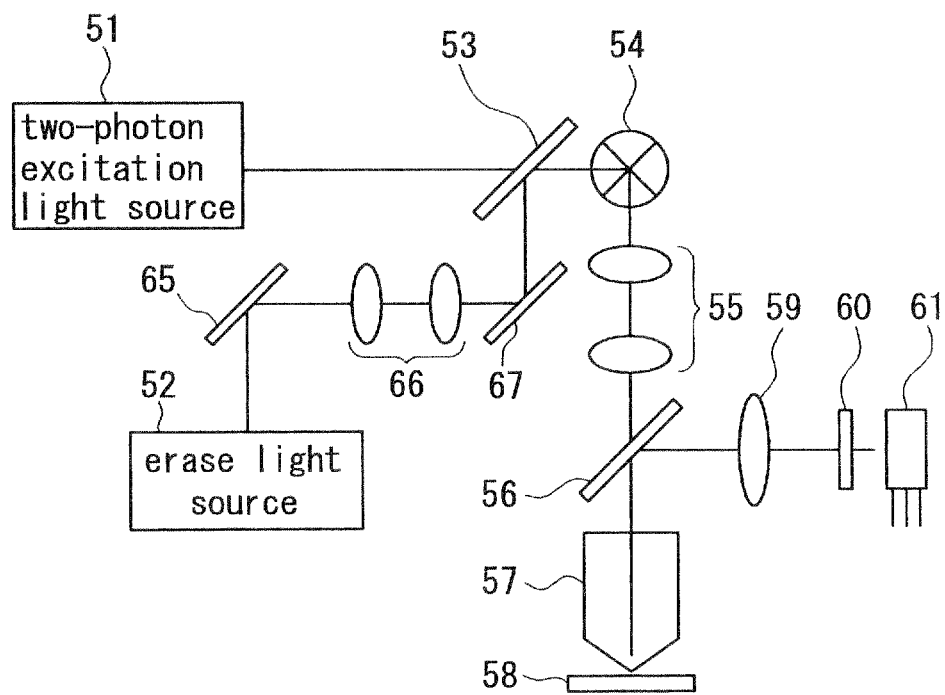
FIG. 5 is a schematic block diagram of a main part of a two-photon microscope according to a third embodiment of the present invention.

A sample stained by a fluorescent dye in a two-photon absorption process is observed with a microscope according to a third embodiment of the present invention. FIG. 5 is a schematic block diagram of a main part of a two-photon microscope according to the present embodiment. This two-photon microscope has a two-photon excitation light source 51 which is a stimulation light source and an erase light source 52. The two-photon excitation light source 51 uses, for example, a titanium sapphire pulsed laser of mode lock type and generates, from the titanium sapphire pulsed laser, pulsed light having relatively high peak power and a pulse width of not more than 10 picoseconds in a relatively wide wavelength range from 900 nm (near-infrared) to 700 nm as pump light (stimulation light). The pump light of this wavelength range excites fluorescent dye having rhodamine, fluoroscein and the like in the molecular skeleton thereof to make the dye generate fluorescence.

The erase light source 52 uses, for example, a red krypton laser and uses laser light having a wavelength of 647 nm emitted therefrom as erase light. The erase light having this wavelength can extremely efficiently suppress fluorescence of rhodamine 6G, for example. The erase light needs to be either pulsed light having a pulse width wider than a pulse width of pump light or a continuous wave.

The pump light emitted from the two-photon excitation light source 51 is transmitted through a dichroic mirror 53 and collected on a sample 58 via a two-dimensional scanner 54, an illumination optical system 55, a dichroic mirror 56 and a microscope objective lens 57. In addition, the fluorescence generated from the sample 58 by irradiation of the pump light is transmitted through the microscope objective lens 57, reflected by the dichroic mirror 56, passed through a collective lens 59 and a ND filter 60 and then received by a photomultiplier tube 61 to be measured.

On the other hand, the erase light emitted from the erase light source 52 is reflected by a dichroic mirror 53 via a movable reflecting mirror 65, adjustment lens system 66 and a movable reflecting mirror 67 and then collected on the sample 58, as is the case with the pump light, via the two-dimensional scanner 54, the illumination optical system 55, the dichroic mirror 56 and the microscope objective lens 57. The movable reflecting mirrors 65, 67 are configured so that the erase light is polarized in the perpendicular directions with each other.

Figure 6:
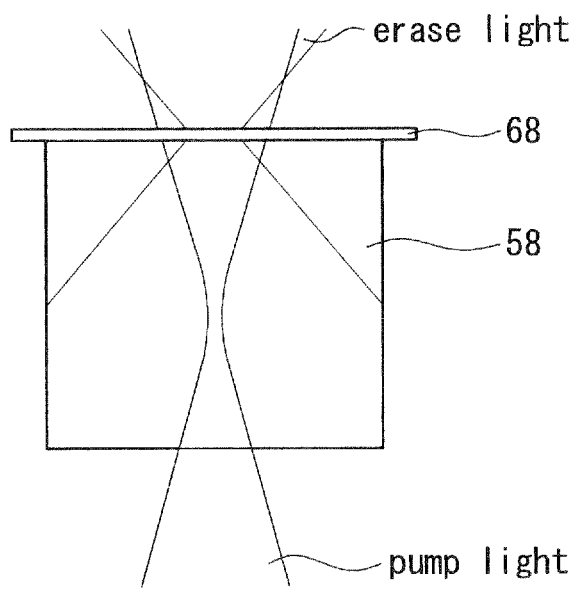
FIG. 6 is a view showing a light-collecting position of pump light and erase light in a two-photon microscope shown in FIG. 5.

The optical axis of the erase light is spatially adjusted by the movable reflecting mirrors 65, 67 completely independently of the pump light and the light-collecting position and size by the microscope objective lens 57 is adjusted by the adjustment lens system 66 so that the light-collecting position of the erase light is determined three-dimensionally independently of the light-collecting position of the pump light. For example, as shown in FIG. 6, in case that the pump light is made to be collected at a deep part of the sample 58, the erase light is made to be collected at the interface between the sample 58 and a cover glass 68, where secondary response light easily occurs by the pump light. Accordingly, the movable reflecting mirrors 65, 67 and the adjustment lens system 66 comprises an adjusting means.

In this way, it is possible to suppress the fluorescence occurring at the cover glass 68 itself, the fluorescence caused by solvent molecules other than a staining dye of the sample 58, and the fluorescence caused by a staining dye in the vicinity of the interface of the cover glass 68. Further, since the pump light is collected at a deep part of the sample 58 away from the light-collecting position of the erase light and only extremely week erase light arrives at this light-collecting area of the pump light, fluorescence suppression is hardly induced therein. Accordingly, since intense background light from the interface between the sample 58 and the cover glass 68, which has been conventionally acknowledged as a problem, can be suppressed, whereby the two-photon fluorescence from the light-collecting area at the deep part of the sample can be detected with a good S/N ratio and three-dimensional depth observation of a biological sample by a two-photon microscope can be achieved.

Since the wavelength of the pump light is different from that of the erase light, it is possible to arrange the illumination optical system 55 and the microscope objective lens 57 such that chromatic aberration is thereby generated and thus the light-collecting positions of the pump light and the erase light are differentiated from each other. In this case, the adjusting means comprises an optical element capable of generating chromatic aberration.

Since a beam diameter of the pump light changes depending on the wavelength thereof, the beam diameter of the pump light can be adjusted by adjusting the illumination optical system 55 placed in a common optical path of the pump light and the erase light or by optionally placing a beam expander so that the beam diameter corresponds to a pupil diameter of the microscope objective lens 57. In this case, although the beam diameter of the erase light is also changed at the same time, the beam diameter of the erase light can be independently adjusted by adjusting the distance between lenses of the adjustment lens system 66. Therefore, for example, the beam diameter of the pump light can be made identical to that of the erase light.

If the beam diameters of the pump light and the erase light are made identical as described above, a convergence angle which defines a passage area of the pump light emitted from the microscope objective lens 57 in the sample 58 can be made identical to a convergence angle of the erase light so that unnecessary fluorescence excitation other than at the light-collecting point can be suppressed reliably and efficiently. Needless to say, if the light-collecting position of the erase light is different from that of the pump light, desired response light is never suppressed. The beam diameter of the pump light may be adjusted by providing a beam expander on a single optical path of the pump light ranging from the two-photon excitation light source 51 to the dichroic mirror 53, rather than carrying out the adjustment on the common optical path.

Fourth Embodiment

Figure 7:
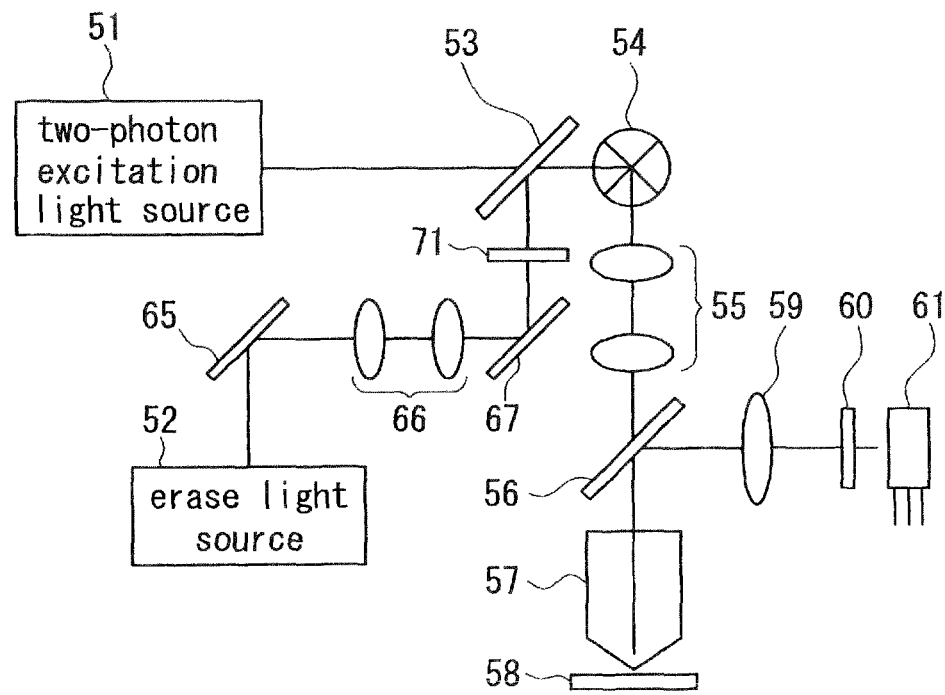
FIG. 7 is a schematic block diagram of a main part of a microscope according to a fourth embodiment of the present invention.
Figure 8:
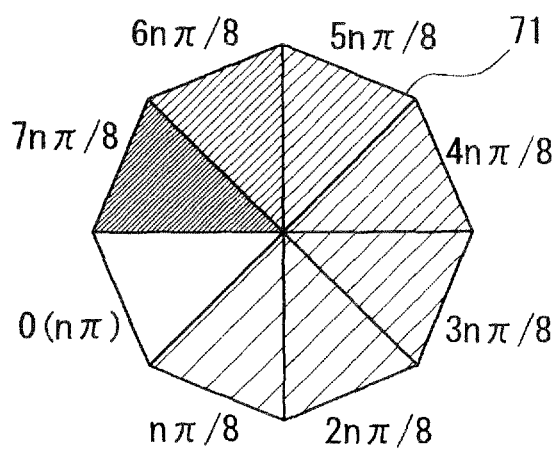
FIG. 8 is a plan view showing a schematic structure of an example of a phase plate shown in FIG. 7.

FIG. 7 is a schematic block diagram of a main part of a two-photon microscope according to a fourth embodiment of the present invention. This two-photon microscope is substantially the same as the two-photon microscope shown in FIG. 5, except that the former comprises a phase plate 71 placed, on the optical path of the erase light, between the erase light source 52 and the dichroic mirror 53. The phase plate 71 is so constructed that phase difference of the erase light varies by $n\pi$ (n is a positive integer of not less than 2) around the optical axis of the erase light. As shown in FIG. 8, for example, the phase plate 71 is formed by etching a glass substrate or by vapor-depositing a transparent thin film on a glass substrate so that there are eight independent regions around the optical axis, whose phases are different from one another by $n\pi/8$.

According to the present embodiment, when the erase light transmitted through the phase plate 71 is collected by the microscope objective lens 57, electric field is cancelled out on the optical axis, whereby the beam has a hollow pattern-like beam shape having a hollow portion in the optical axis direction (i.e. doughnut shape), more specifically a capsule-like beam shape (three-dimensional dark hall shape) or a tube-like beam shape (macaroni-like shape). Therefore, when the pump light and the erase light are coaxially combined and the pump light is collected at the hollow portion of the erase light, no erase light is irradiated in the light-collecting area of the pump light but erase light is irradiated around the light-collecting area, whereby fluorescence is suppressed. Accordingly, as shown in FIG. 6, by appropriately setting the light-collecting position of the erase light at the interface between the sample 58 and the cover glass 68 or the like where secondary response light easily occurs, fluorescence in the light-collecting area of the pump light can be measured with a relatively higher S/N ratio.

In addition, in the present embodiment, it is preferable to design the phase plate 71 so that phase difference of the erase light varies around the optical axis thereof by not less than $3\pi$ or thin the beam diameter of the erase light, thereby enlarging the diameter of the hollow portion of erase light at the light-collecting portion, to ensure that the light-collecting spot of the pump light is located sufficiently inside of the hollow portion of the erase light.

Fifth Embodiment

Figure 9:
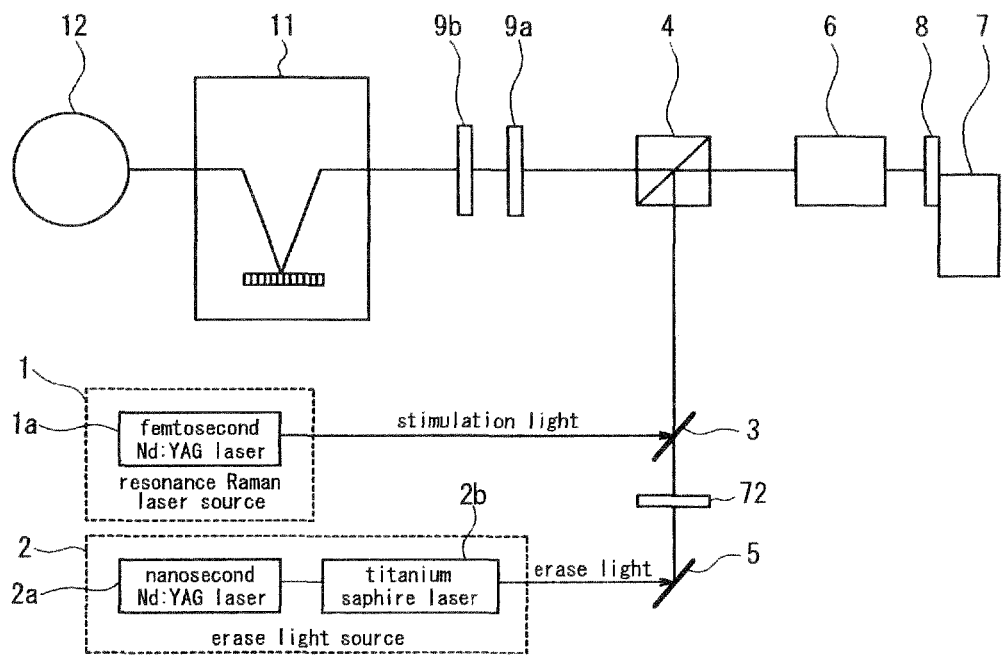
FIG. 9 is a schematic block diagram of a main part of a scanning resonance Raman laser microscope according to a fifth embodiment of the present invention.

FIG. 9 is a schematic block diagram of a main part of a scanning resonance Raman laser microscope according to the fifth embodiment of the present invention. This scanning resonance Raman laser microscope is substantially the same as the scanning resonance Raman laser microscope shown in FIG. 3, except that the former comprises a phase plate 72 having the same configuration as that shown in FIG. 8 and placed, on the optical path of the erase light, between the reflecting mirror 5 and the dichroic mirror 3. The scanning resonance Raman laser microscope of the present embodiment is designed such that the erase light irradiated on the biological sample 8 has a hollow shape and Raman process-inducing stimulation light is collected on the hollow portion.

Therefore, according to the present embodiment, since no erase light is irradiated in the light-collecting area of Raman process-inducing stimulation light, the scanning resonance Raman laser microscope can detect a resonance Raman signal generated by the Raman process-inducing stimulation light without being affected by irradiation of the erase light, whereby detection precision is improved.

Sixth Embodiment

Figure 10:
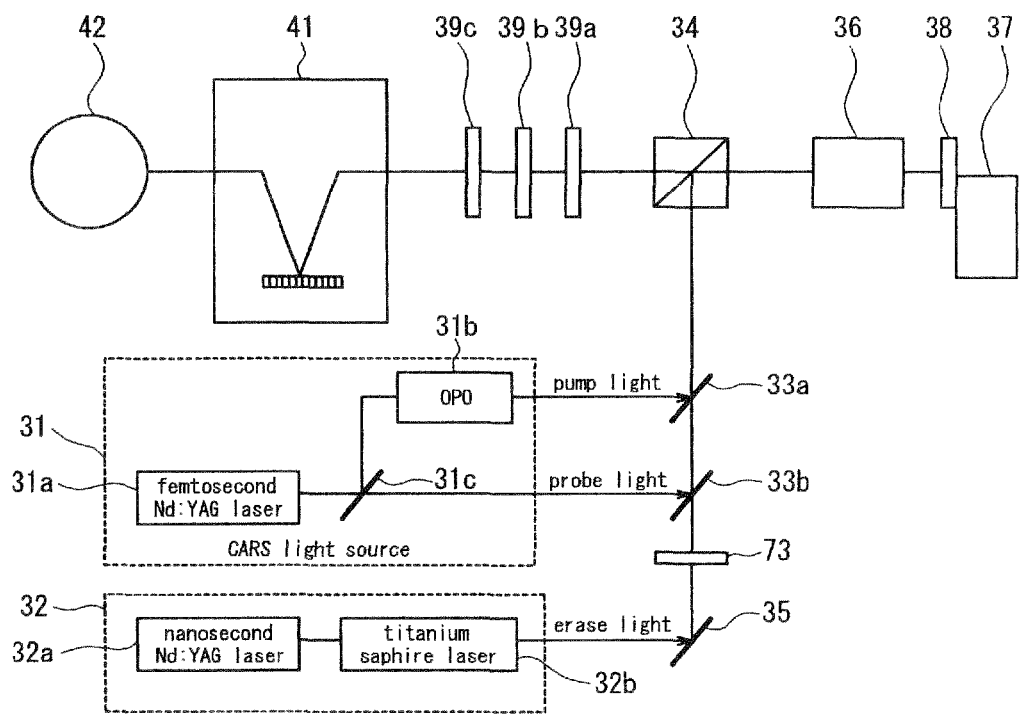
FIG. 10 is a schematic block diagram of a main part of a CARS microscope according to a sixth embodiment of the present invention.

FIG. 10 is a schematic block diagram of a main part of a CARS microscope according to a sixth embodiment of the present invention. The CARS microscope is substantially the same as the CARS microscope shown in FIG. 4, except that the former comprises a phase plate 73 having the same configuration as that shown in FIG. 8 and placed, on the optical path of the erase light, between the reflecting mirror 35 and the dichroic mirror 33b. The CARS microscope of the present embodiment is designed such that the erase light irradiated on the biological sample 38 has a hollow shape and the pump light and the probe light are collected at the hollow portion.

Thus, according to the present embodiment, since no erase light is irradiated in the light-collecting areas of the pump light and the probe light, Raman spectrum of the biological sample 38 can be observed without being affected by the irradiation of the erase light, whereby detection precision of environmentally responsive fluoroprobe is improved.

Seventh Embodiment

Figure 11:
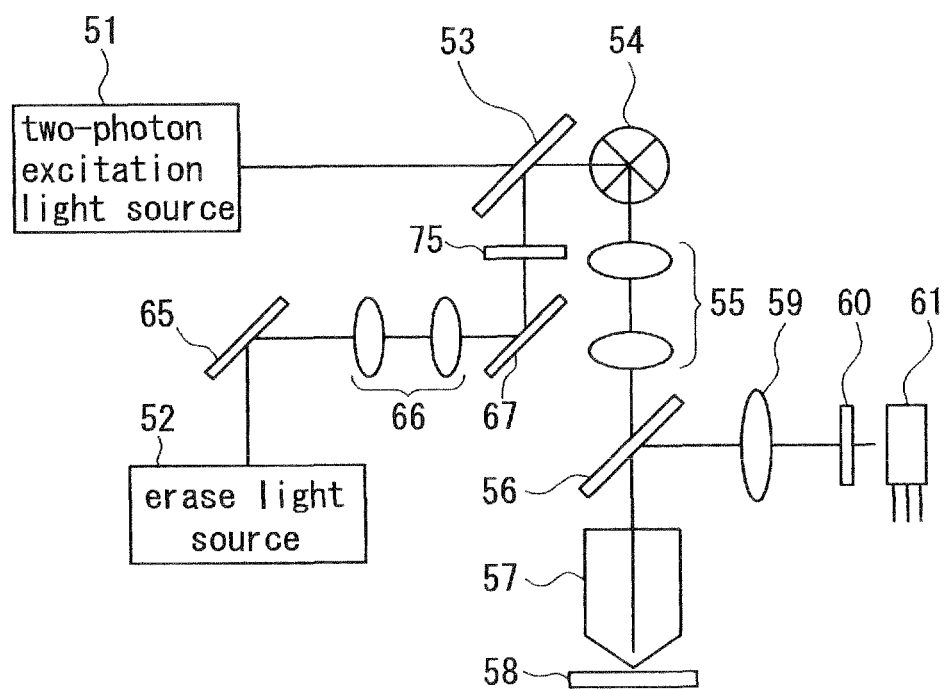
FIG. 11 is a schematic block diagram of a main part of a two-photon microscope according to a seventh embodiment of the present invention.

FIG. 11 is a schematic block diagram of a main part of a two-photon microscope according to a seventh embodiment of the present invention. This two-photon microscope is substantially the same as the two-photon microscope shown in FIG. 7, except that the phase plate 71 of the former is replaced with a wavefront modulation element 75 placed, on the optical path of the erase light, between the erase light source 52 and the dichroic mirror 53. The wavefront modulation element 75 comprises, for example, a transmissive liquid crystal element (Liquid Crystal Display: LCD), a lens for generating spherical aberration, a phase plate or the like. In the structure above, by modulating (disturbing) the wavefront of the erase light and deteriorating the light-collecting performance of the erase light, the peak power at the light-collecting position is reduced.

Specifically, by disposing the wavefront modulation element 75 on the optical path of the erase light to decrease the peak power at the light-collecting position, it is possible to prevent the erase light from suppressing emission of desired response light and thus effectively suppress only the unnecessary response light. As a result, desired response light can be detected with a good S/N ratio.

Although the wavefront modulation element 75 is independently provided on the optical path of the erase light in FIG. 11, it is possible to provide another optical element with the function of the wavefront modulation element 75 and omit the wavefront modulation element 75. The movable reflecting mirror 65 or 67, for example, comprises a reflective liquid crystal element (Liquid Crystal On Silicon: LCOS) or an MEMS deformable mirror so that it also serves as a wavefront modulation element. Further, it is possible to structure the adjustment lens system 66 so as to function as a wavefront modulation element, as well, by providing the adjustment lens system 66 with spherical aberration or making the curvature of the adjustment lens system relatively small or generating aberration in the adjustment lens system 66 by eccentrically or obliquely placing the adjustment lens system 66. Or, the wavefront modulation element may configured by intentionally generating a factor which generally deteriorates light-collecting performance by, for example, intentionally reducing surface precision of optical members or inserting an element of low optical precision.

Eighth Embodiment

Figure 12:
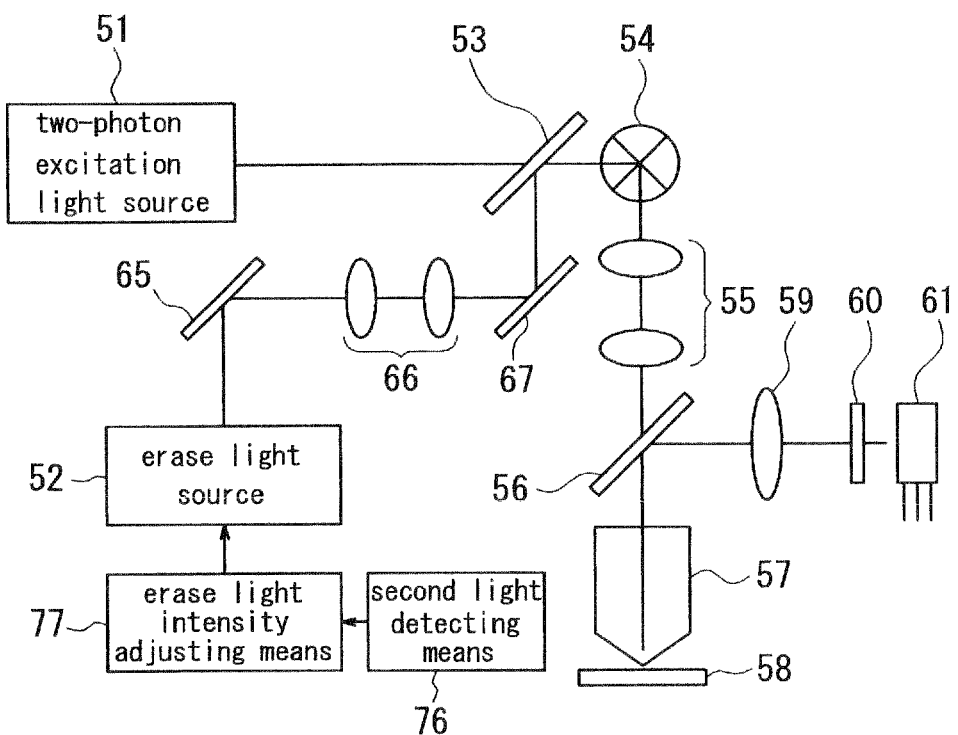
FIG. 12 is a schematic block diagram of a main part of a two-photon microscope according to an eighth embodiment of the present invention.

FIG. 12 is a schematic block diagram of a main part of a two-photon microscope according to an eighth embodiment of the present invention. This two-photon microscope is substantially the same as the two-photon microscope shown in FIG. 5, except that the former further comprises a secondary light detecting means 76 for detecting secondary response light occurring at the surface of the sample 58 and an erase light intensity adjusting means 77 for adjusting intensity of the erase light emitted from the erase light source 52 based on the output of the secondary light detecting means 76.

Figure 13:
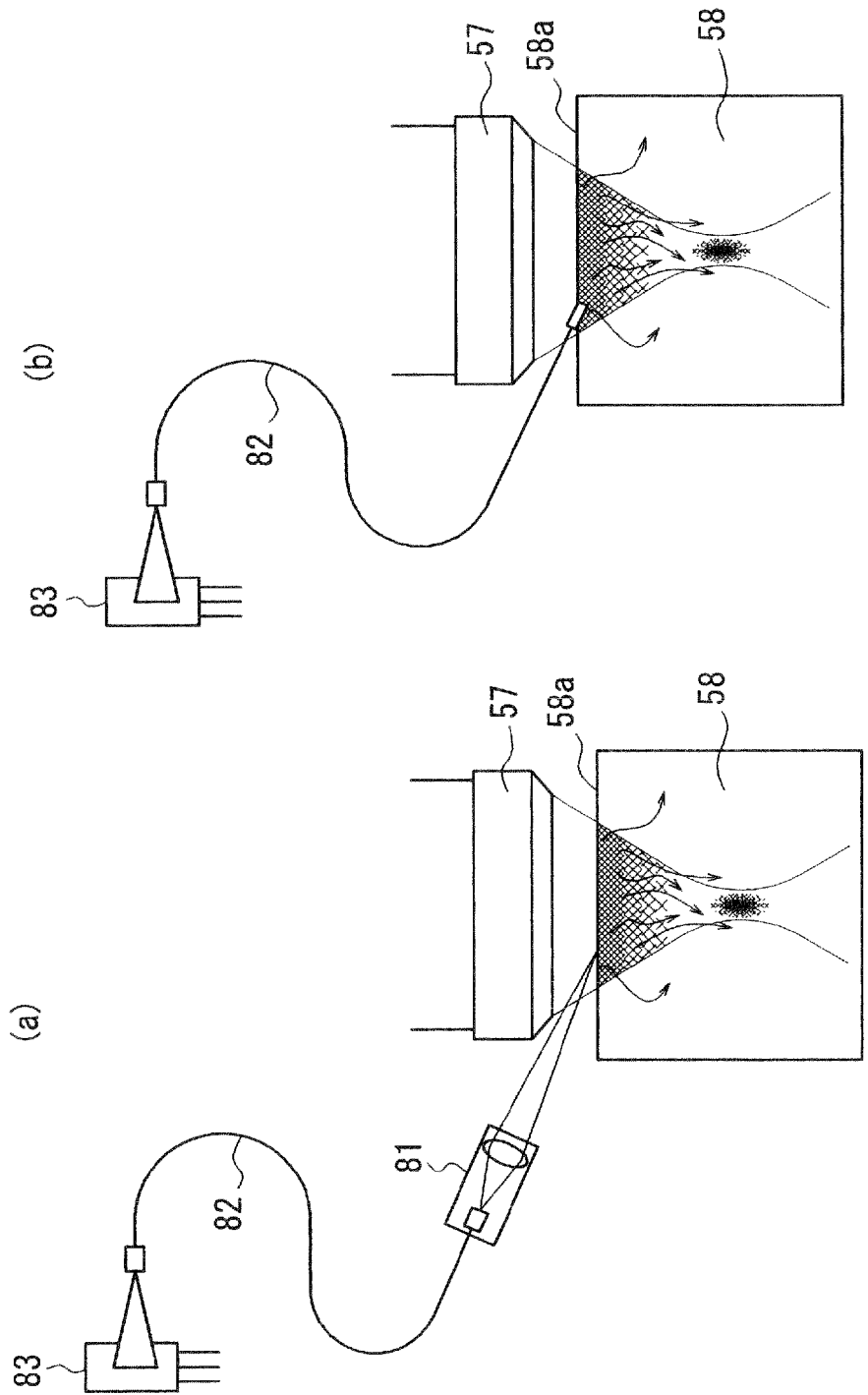
FIG. 13 is a view showing two examples of a secondary light detecting means shown in FIG. 12.

The secondary light detecting means 76 can be configured as shown in FIG. 13(a) or 13(b). In FIG. 13(a), the secondary response light occurring at the surface 58a of the sample 58 is collected by a detection optical system 81 including a collective lens, passed through an optical fiber 82 and detected with a photodetector 83 such as a photomultiplier tube. In FIG. 13(b), the optical fiber 82 is supported by a manipulator (not illustrated) to contact the surface 58a of the sample 58 such that the secondary response light occurring at the surface 58a of the sample 58 is directly detected by the photodetector 83 via the optical fiber 82.

The erase light intensity adjusting means 77 adjusts the intensity of the erase light emitted from the erase light source 52, based on the output of the secondary light detecting means 76, to minimize the output of the second detecting means 76, for example.

In this way, by directly detecting the secondary response light occurring at the surface of the sample 58 and adjusting the intensity of the erase light, it is possible to effectively suppress unwanted response light due to both stimulation light and erase light. Accordingly, it is possible to detect desired response light with a higher S/N ratio. In addition, such a configuration for adjusting erase light intensity as described above can be effectively applied to each of the above-mentioned embodiments.

Ninth Embodiment

Figure 14:
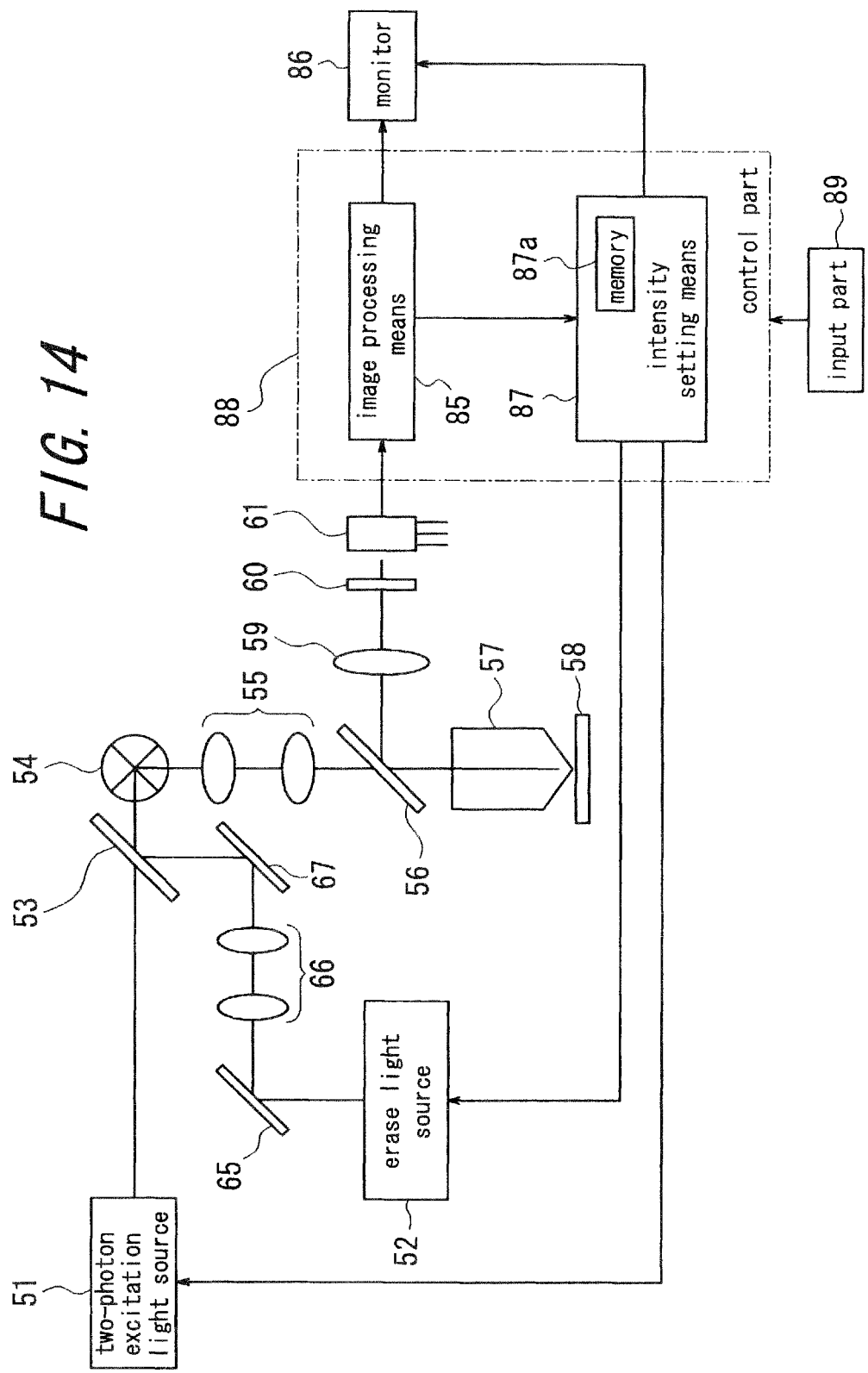
FIG. 14 is a block diagram of a main part of a two-photon microscope according to a ninth embodiment of the present invention.

FIG. 14 is a schematic block diagram of a main part of a two-photon microscope according to a ninth embodiment of the present invention. This two-photon microscope is substantially the same as the two-photon microscope shown in FIG. 5, except that the former comprises: an image processing means 85 for receiving the output of the photomultiplier tube 61 constituting a response light detecting means and generating an image signal to show spatial intensity distribution of the response light from the sample 58; a monitor 86 for receiving the image signal generated by the image processing means 85 and displaying an image; and an intensity setting means 87 for setting intensity of the erase light emitted from the erase light source 52 based on the image signal generated by the processing means 85. The image processing means 85 and the intensity setting means 87 are a part of a controller 88 having a personal computer for controlling the total operation of the two-photon microscope. Further, an input part 89 consisting of a keyboard or the like is connected to the controller 88.

Hereinafter, an example of an operation when sample 58 is observed by the two-photon microscope as shown in FIG. 14 will be described.

Figure 15:
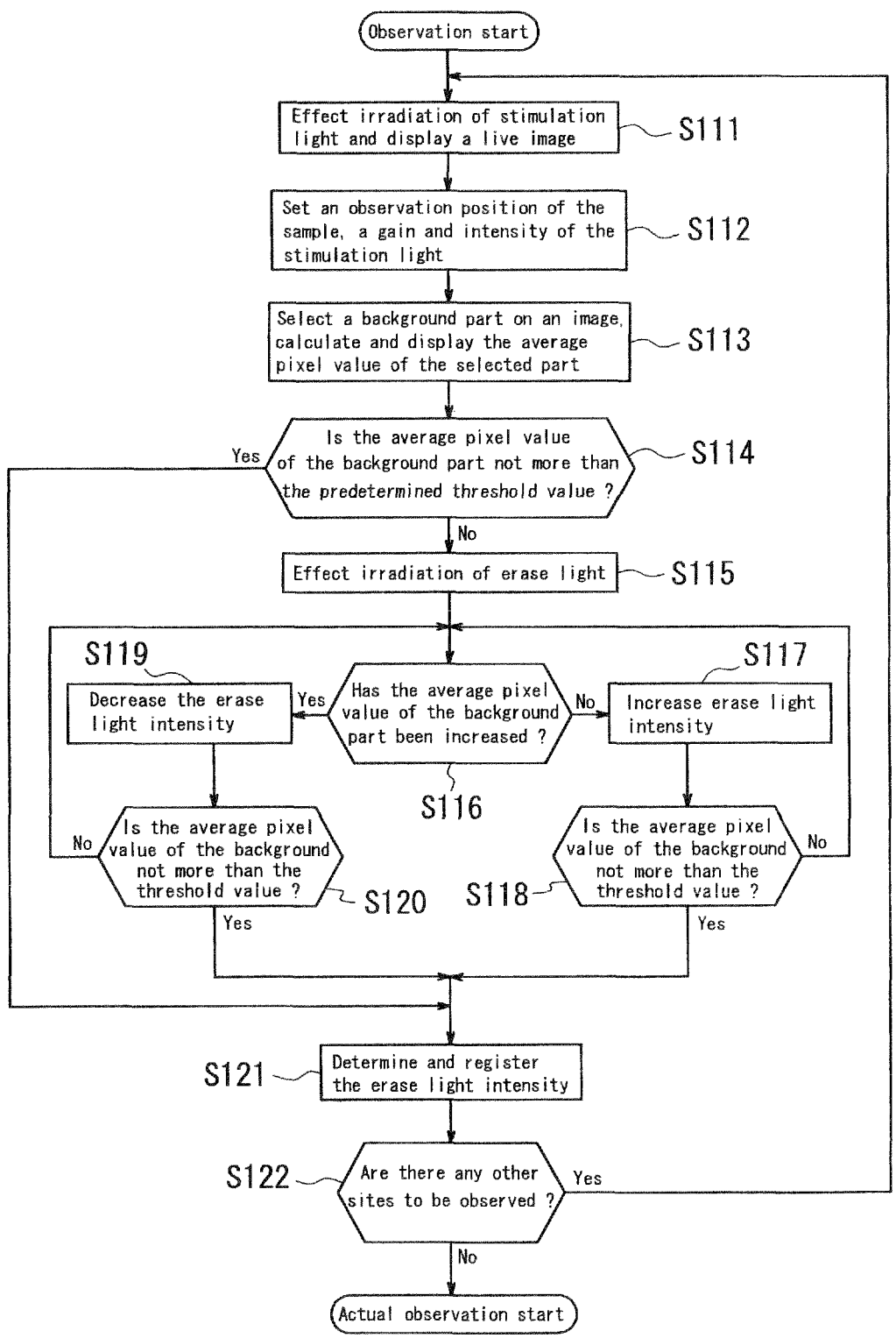
FIG. 15 is a flow chart for explaining the first operation example of the two-photon microscope shown in FIG. 14.

FIG. 15 is a flow chart for explaining the first operation example. In this operation example, at first, irradiation of stimulation light (pump light) on the sample 58 is started and a live image of the sample 58 by the response light is displayed on the monitor 86 (in step S111). Next, an observation position of the sample 58, a gain (an amplification factor) of the photomultiplier tube 61 and intensity of the stimulation light are set (in step S112).

When the above-mentioned processes are completed, the intensity setting means 87 selects a background part on the image based on an image signal provided from the image processing means 85, calculates the average pixel value of pixel signals (pixel values) of the selected part and displays the result on the monitor 86 (in step S113). Thereafter, the intensity setting means 87 judges whether the average pixel value of the background part is not more than the predetermined threshold value or not (in step S114). As a result of step S114, when the average pixel value of the background part exceeds the threshold value, that is, a noise by secondary response light is large, irradiation of the erase light is started (in step S115). Thereafter, the intensity setting means 87 similarly calculates the next average pixel value of the background part to judge whether or not the next average pixel value has been increased, as compared with the previous average pixel value (in step S116).

As a result, when the next average pixel value has not been increased (i.e. when "No" in step S116), in other words, when the average pixel value has been decreased or remains the same, the intensity setting means 87 increases the erase light intensity by a predetermined value of change (in step S117). Thereafter, the intensity setting means 87 similarly calculates the yet next average pixel value of a background part to judge whether the yet next average pixel value is not more than the predetermined threshold value or not (in step S118). In contrast, when the next average pixel value has been increased (i.e. when "Yes" in step S116), the intensity setting means 87 decreases the erase light intensity by a predetermined value of change (in step S119). Thereafter, the intensity setting means 87 similarly calculates the yet next average pixel value of the background part to judge whether the yet next average pixel value is not more than the predetermined threshold value or not (in step S120).

In a case where the average pixel value of the background part exceeds the threshold value in step S118 or in step S120, the procedure goes to step S116 and the above-described operations are repeated. In contrast, in a case where the yet next average pixel value of the background part is not more than the threshold value in step S118 or in step S120, erase light intensity at that time is determined (set) as intensity at the observation position, that is, intensity at the corresponding relative position of the microscope objective lens 57 with respect to the sample 58 (a light-collecting position of the pump light in the depth direction of the sample 58) and registered (stored) in a built-in memory 87a (in step S121).

Thereafter, it is judged whether there are other observation parts or not (in step S122). If yes, the procedure goes to step S111 and the above-described steps are repeated. If no, actual observation (image acquisition) is started.

In step S114, when the average pixel value of the background part is less than the predetermined threshold value, that is, a noise by the secondary response light is so small that the desired response light can be detected with a good S/N ratio, the process goes to step S121 without effecting irradiation of the erase light and it is recorded in the memory 87a that irradiation of erase light is not performed at the particular observation position.

When the erase light intensity at the observation position has been stored in the memory 87a as described above, actual observation of the sample 58 is started by reading out the corresponding erase light intensity in accordance with the relative position of the microscope objective lens 57 with respect to the sample 58. With this, unwanted response light due to both of the stimulation light (pump light) and the erase light is suppressed and thus desired response light can be detected with a good S/N ratio.

Figure 16:
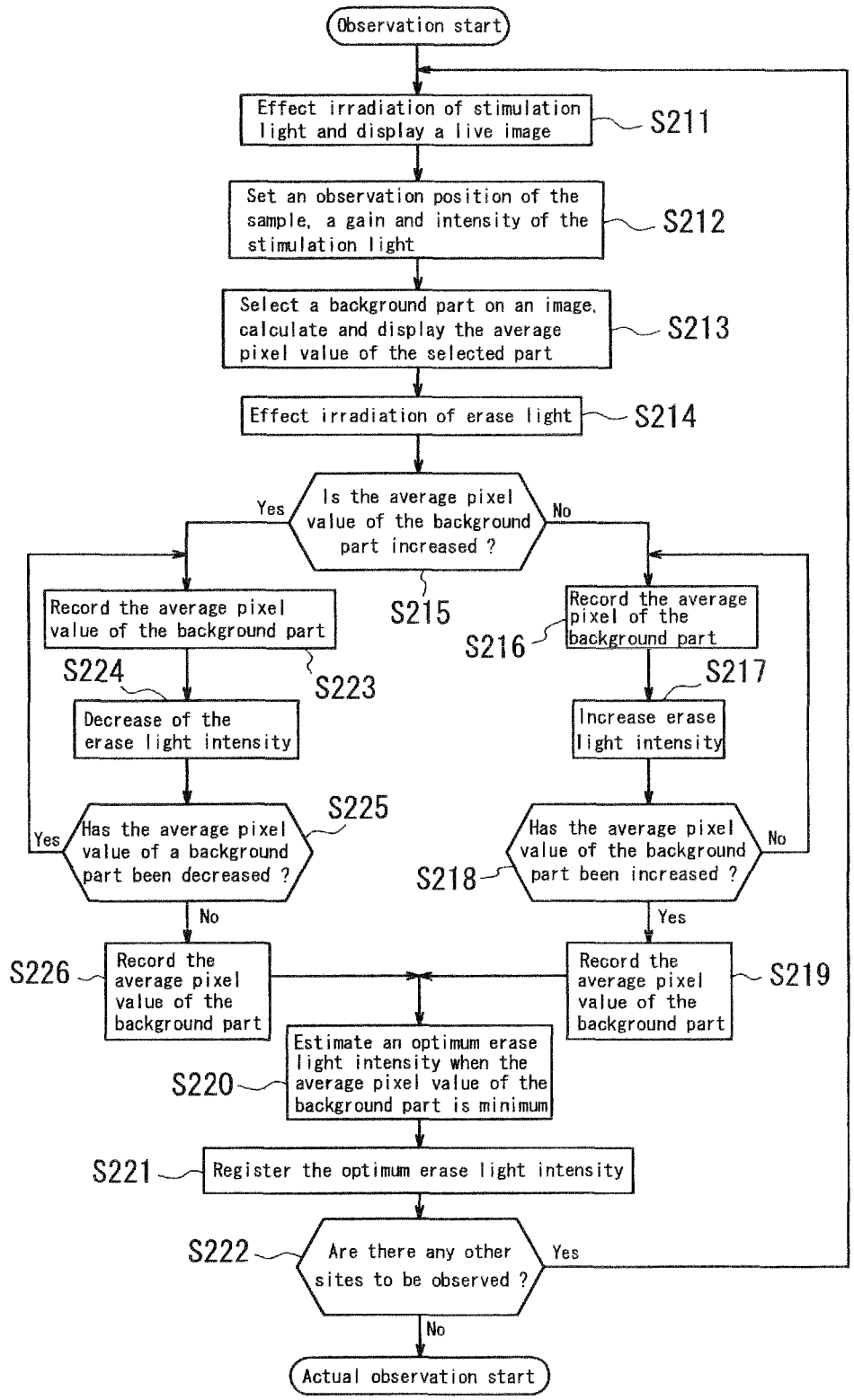
FIG. 16 is a flow chart for explaining the second operation example of the two-photon microscope shown in FIG. 14.

FIG. 16 is a flow chart for explaining the second operation example. In this operation example, steps S211 to S213 are the same as steps S111 to S113 in FIG. 15. When the process in step S213 is completed, the intensity setting means 87 starts irradiation of the erase light (step S214), and then calculates the average pixel value of the background part as in step S213 to judge whether or not the average pixel value has been increased, as compared with the previous average pixel value calculated prior to irradiation of the erase light (in step S215).

Figure 17:
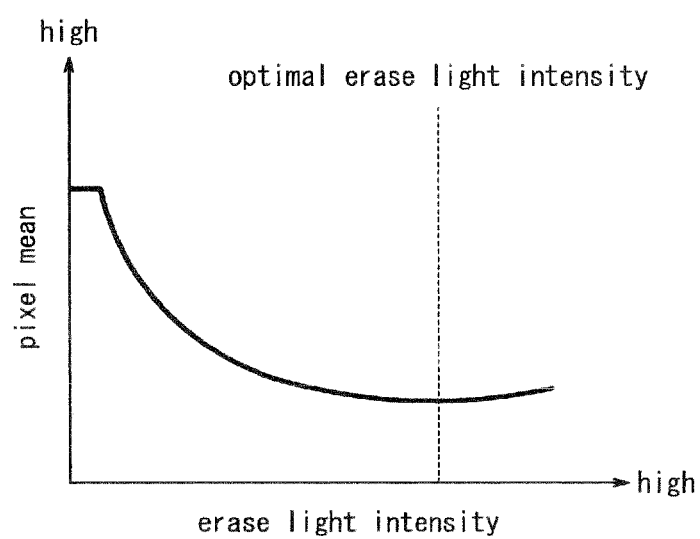
FIG. 17 is a view showing the relation between erase light intensity and a average pixel value in the second operation example shown in FIG. 16.

As a result, in a case where the average pixel value has not been increased (when "No" in step S215), that is, when the average pixel value has been decreased or remains the same, it is understood that the erase light is working and there is a possibility that background light may be further suppressed. In this case, at first the calculated average pixel value of the background part, together with the erase light intensity at that time, is stored in the memory 87a (in step S216). Afterwards, the intensity setting means 87 increases the erase light intensity by a predetermined value of change (in step S217) and similarly calculates the next average pixel value of the background to judge whether the next average pixel value has been increased or not, as compared with the previous average pixel value (in step S218). As a result, in the case where the yet next average pixel value has been decreased or remains the same, the procedure goes to step S216 and the processes from step S216 to step S218 are repeated. In contrast, in the case where the yet next average pixel value has been increased, the average pixel value thus increased of the background part at present is stored in the memory 87a together with the erase light intensity (in step S219). Accordingly, in this case, for example, the average pixel value of the background part with respect to the erase light intensity as shown in FIG. 17 is stored in the memory 87a.

Next, the intensity setting means 87 estimates an optimum erase light intensity, at which the average pixel value of the background part is minimum, based on the information stored in the memory 87a (in step S220) and stores the estimated optimum erase light intensity in a predetermined region of the memory 87a (in step S221).

Thereafter, it is judged whether there are other sites to be observed or not (in step S222). If yes, the procedure goes to step S211 and the above-mentioned steps are executed. If no, the procedure is completed.

In step S215, when the average pixel value of the background part has been increased by the irradiation of the erase light (i.e. when "Yes" in step S215), it is assumed that the erase light intensity is so high that two-photon excitation by the erase light has occurred, making the erase light itself a cause of background light. In this case, as in S216, the calculated average pixel value of the background part is stored in the memory 87a together with the erase light intensity at that time (in step S223). Afterward, the intensity setting means 87 decreases the erase light intensity by a predetermined value of change (in step S224). The intensity setting means 87 then similarly calculates the next average pixel value of the background to judge whether the next pixel average value has been decreased or not, as compared with the previous average pixel value (in step S225). As a result, in the case that the average pixel value has been decreased, the procedure goes to step S223 and the processes from step S223 to step S225 are repeated. In contrast, in the case that the average pixel value has been increased, the increased average pixel value of the background part is stored in the memory 87a together with the erase light intensity at that time (in step S226).

Thereafter, the intensity setting means 87 estimates the optimum erase light intensity, at which the average pixel value of the background part is minimum, based on the information stored in the memory 87a in step S220 and stores the estimated optimum erase light intensity in a predetermined region of the memory 87a in step S221. Thereafter, it is judged in step S222 whether there are other sites to be observed or not. If yes in step S222, the procedure goes to step S211 and the above-mentioned processes are executed. If no in step s222, the procedure is completed.

When the optimum erase light intensity at the observation position is stored in the memory 87a as described above, actual observation (image acquisition) of the sample 58 is started by reading out the corresponding optimum erase light intensity in accordance with the relative position of the microscope objective lens 57 with respect to the sample 58. With this, unwanted response light due to both of the stimulation light (pump light) and the erase light is suppressed and thus desired response light can be detected with a good S/N ratio.

Figure 18:
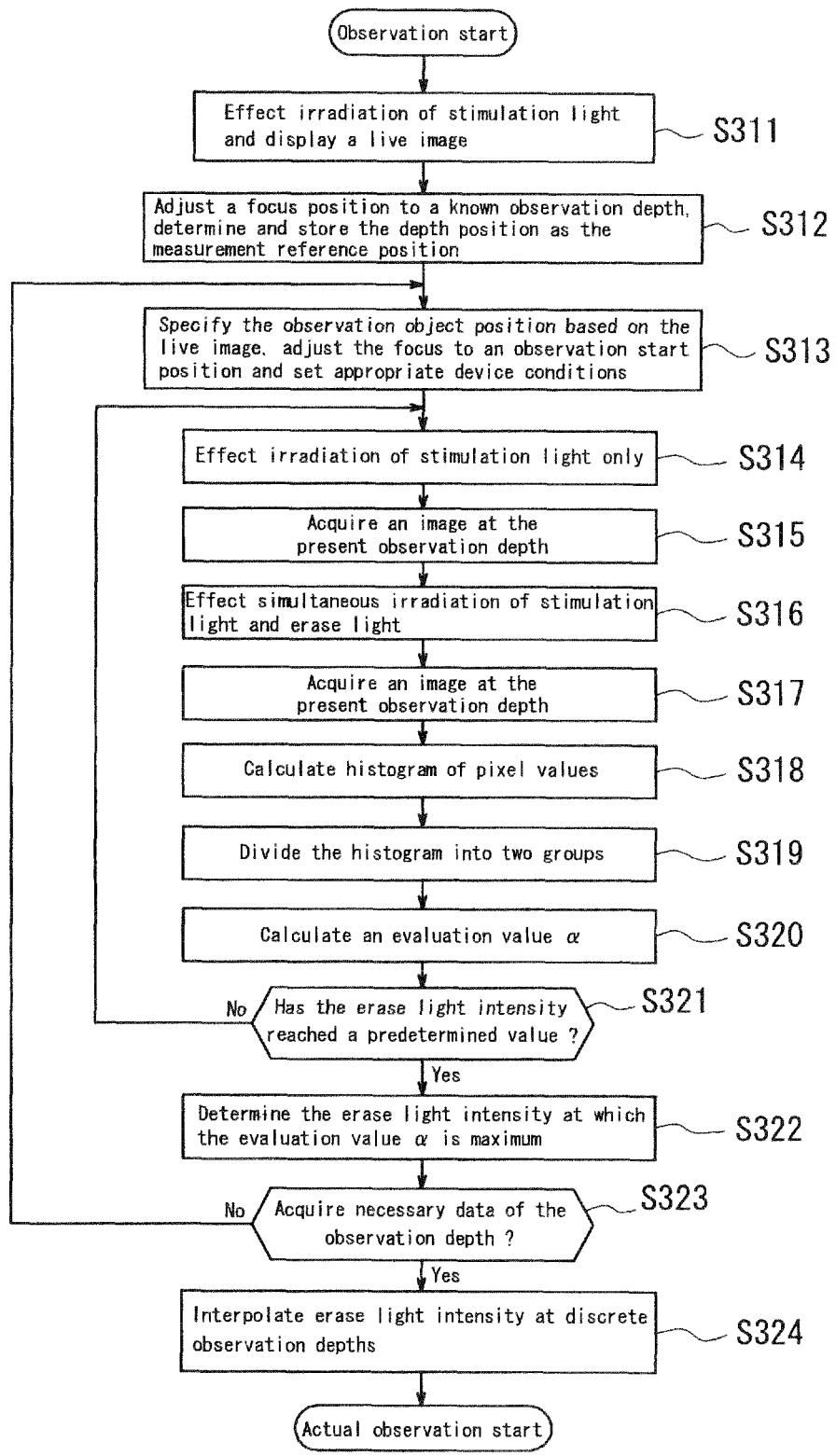
FIG. 18 is a flow chart for explaining the third operation example of the two-photon microscope shown in FIG. 14.

FIG. 18 is a flow chart for explaining a third operation example. In this operation example, at first irradiation of the stimulation light (pump light) on the sample 58 is started and a live image of the sample 58 by response light is displayed on the monitor 86 (in step S311). Next, a focus position of the microscope objective lens 57 is adjusted to a known observation depth (for example, a sample surface, a cover glass surface and the like) and the depth position corresponding to the focus position is set as the measurement reference position to be stored in the memory 87a (in step S312).

Afterward, the observation object position (range) is specified based on the live image, the focus of the microscope objective lens 57 is adjusted to a depth at which observation is started, and other device conditions are set in an appropriate manner (in step S313). Examples of the device conditions to be set include a gain (an amplification factor) of the photomultiplier tube 61, an offset, stimulation light intensity, scan speed of the two-dimensional scanner 54, an image size, a size of an observation field of view and the like.

Next, the intensity setting means 87 effects a state where only stimulation light is being irradiated (in step S314) and acquires an image at the current observation depth in the state and stores image data of the acquired image in the memory 87a (in step S315). Afterward, simultaneous irradiation of the stimulation light and the erase light is started (in step S316). The intensity setting means 87 then acquires an image at the current observation depth and stores image data of the image thus acquired in the memory 87a (in step S317).

Next, the intensity setting means 87 selects the whole image or a part of the image area with respect to each of the images obtained as a result of the irradiation of only the acquired stimulation light and the irradiation of both of the stimulation light and the erase light, and calculates histogram of pixel values included in the selected image area (in step S318). The histogram thus calculated is displayed on the monitor 86 according to necessity. Afterwards, the intensity setting means 87 divides the calculated histogram of each image into two groups, one including larger pixel values than a predetermined threshold value and the other including smaller pixel values than the threshold value (in step S319).

The threshold value for dividing histogram is either automatically set by calculating the average value of pixel values of all pixels or arbitrarily set by confirming the histogram displayed on the monitor 86 by an operator through the input part 89. It is preferable to use the average value of all pixel values of the former (automatic setting) in a case where the sample 58 is nervous system of a living body.

Afterwards, the intensity setting means 87 calculates an evaluation value $\alpha$ to show a S/N ratio of the image obtained by simultaneous irradiation of the stimulation light and the erase light (in step S320) based on the divided histogram of each image.

Accordingly, the intensity setting means 87, with respect to the image acquired by simultaneous irradiation of the stimulation light and the erase light, calculates the average value of pixel values in each group of the divided histogram and assumes the average pixel value of one group having pixel values of not less than the threshold value as desired response light component A, and the average pixel value of the other group having pixel values of less than the threshold value as noise component B. Further, in step S315, in order to correct an influence of color fading of the sample caused by irradiation of the stimulation light during adjustment of erase light intensity, the intensity setting means 87 calculates, with respect to the image acquired by irradiation of only the stimulation light (with no irradiation of the erase light), as well, the average pixel value in each group of divided histogram and assumes the average pixel value of one group having pixel values of not less than the threshold value as desired response light component A' and the average pixel value of the other group having pixel values of less than the threshold value as noise component B'. Further, the intensity setting means 87 acquires in advance desired response light component $A'_0$ and noise components $B'_0$ with respect to the image obtained by irradiation of only the stimulation light calculated before irradiation of the erase light.

The intensity setting means 87 calculates the evaluation value $\alpha$ by the formula: $\alpha=(A/B)/\{(A'_0/A')/(B'_0/B')\}$, where $A'_0/A$ represents influence (change in time) of color fading of a desired response light component and $B'_0/B'$ represents influence (change in time) of color fading of noise components.

Afterwards, the intensity setting means 87 repeats the processes of the above-mentioned steps S314 to S320 until the erase light intensity reaches the predetermined value stored in the memory 87a (in step S321) by changing the erase light intensity to calculate the evaluation value $\alpha$ in each erase light intensity. When the erase light intensity has reached the predetermined intensity, the intensity setting means 87 decides (sets) the erase light intensity at which the evaluation value $\alpha$ is maximum and stores the information in the memory 87a by relating the information to at least one of image acquisition conditions such as the stimulation light intensity, observation depth and the like (step S322).

Next, the intensity setting means 87 judges whether necessary data of the observation depth has been acquired or not (in step S323). If it is has not been acquired, the procedure goes to step S313 and the above-mentioned processes are repeated. In contrast, if necessary data of the observation depth has been acquired, erase light intensity between these depths is interpolated by optionally using an arbitrary function, based on data of erase light intensity with respect to discrete observation depths, and the result is stored in the memory 87*a* (in step S324).

In this way, erase light intensity and image acquisition condition, in which the S/N ratio is the maximum, are stored in the memory 87*a* for each observation depth of the sample 58. Actual observation (image acquisition) of the sample 58 is then started on the basis of the erase light intensity and image acquisition condition for each observation depth thus stored. With this, damage of the sample 58 caused by excessive irradiation of erase light thereon is reduced, whereby desired response light with a good S/N ratio, in which unnecessary response light due to both of the stimulation light (pump light) and the erase light is suppressed, can be detected.

Figure 19:
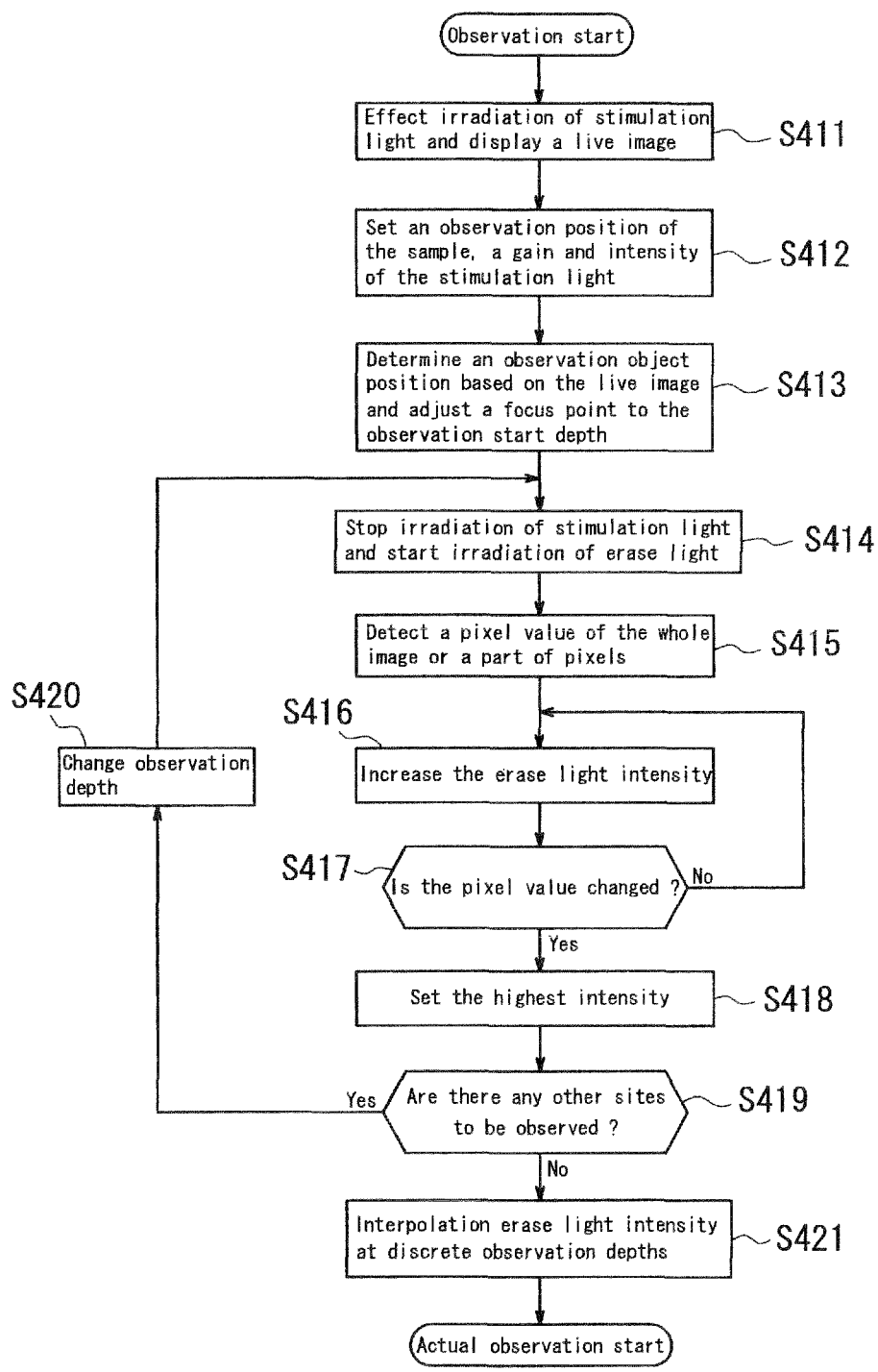
FIG. 19 is a flow chart for explaining the fourth operation example of the two-photon microscope shown in FIG. 14.

FIG. 19 is a flow chart for explaining a fourth operation example. This operation example is substantially the same as the first to third operation examples, except that the former is configured that intensity of the erase light irradiated on the sample 58 is set not more than the pre-acquired highest intensity, under which a secondary light emission phenomenon does not occur by irradiation of the erase light. In view of this, as in step S311 and step S312 shown in FIG. 18, at first the stimulation light (pump light) starts to be irradiated on the sample 58 and a live image of the sample 58 by the response light is displayed on the monitor 86 (in step S411). Next, a focus position of the microscope objective lens 57 is adjusted to the known observation depth (for example, the sample surface, the cover glass surface and the like), and the position depth is regarded as the measurement reference position and stored in the memory 87*a* (in step S412). Thereafter, an observation object position (range) is determined based on the live image and a focus of the microscope objective lens 57 is set at the depth at which observation is started (in step S413).

Next, the intensity setting means 87 stops irradiation of the stimulation light and starts irradiation of the erase light (in step S414) to detect a pixel value of the whole image or a part of pixels (in step S415). Thereafter, the intensity setting means 87 increases the erase light intensity by a predetermined value of change (in step S416) to judge whether the pixel value changes or not (in step S417). As a result, if the pixel value is not changed, the procedure goes to step S416 and the intensity setting means 87 further increases the erase light intensity by the value of change.

In contrast, if the pixel value is changed in step S417, it is understood that a secondary light emission phenomenon has occurred due to irradiation of the erase light. Therefore, the erase light intensity immediately before the pixel value is changed is set as the highest intensity of the irradiation limit and stored in the memory 87*a* together with information of the observation depth of this case (in step S418).

Next, the intensity setting means 87 judges whether there are other sites to be observed or not (in step S419). If there is another site to be observed, the observation depth is changed (in step S420) and the procedure goes to step S414, repeating the above-mentioned processes. In contrast, if there are no other sites to be observed, erase light intensity between these depths is interpolated by optionally using an arbitrary function, based on data of erase light intensity with respect to discrete observation depths, and the result is stored in the memory 87*a* (in step S421).

In this way, the highest erase light intensity, under which a secondary light emission phenomenon does not occur by irradiation of the erase light, is stored in the memory 87*a* for each observation depth of the sample 58. Actual observation (image acquisition) of the sample 58 is then started by irradiating erase light at or under the stored highest intensity of the erase light for every observation depth. With this, damage of the sample 58 caused by excessive irradiation of erase light thereon is reduced, whereby desired response light with a good S/N ratio, in which unnecessary response light due to both of the stimulation light (pump light) and the erase light is suppressed, can be detected.

It is noted that the above-mentioned first to fourth operation examples are not limited to a two-photon microscope but may be appropriately applied to other microscopes explained in the foregoing embodiments. Further, processes such as in steps S112, S212, S312, S412 and the like in the above-mentioned operation examples are appropriately executed based on input information by an operator though the input 89. Yet further, the operation of setting the erase light intensity in the first operation example may be carried out by an operator effecting the setting through the input portion 89 such that the background intensity is minimum, while observing an image displayed on the monitor 86. Furthermore, the erase light intensity may be set not only in the depth direction (Z-direction) of the sample 58 but also in the X-direction or Y-direction perpendicular to the Z-direction in an XY plane.

Tenth Embodiment

Figure 20:
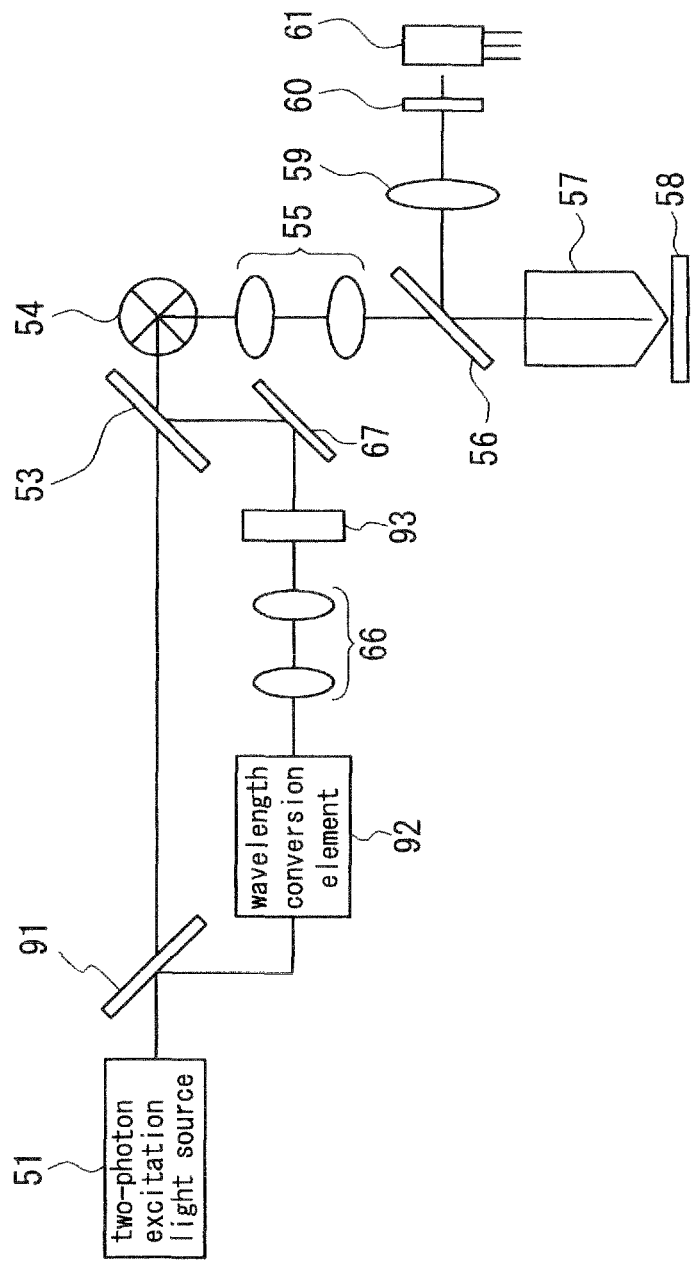
FIG. 20 is a schematic block diagram of a main part of a two-photon microscope according to a tenth embodiment of the present invention.

FIG. 20 is a schematic block diagram of a main part of a two-photon microscope according to a tenth embodiment of the present invention. This two-photon microscope is substantially the same as the two-photon microscope shown in FIG. 5, except that in the former the erase light source 52 is omitted and a part of the stimulation light emitted from the two-photon excitation light source 51 is wavelength-converted to be used as erase light.

Accordingly, in the two-photon microscope according to the present embodiment, pulsed light emitted from the two-photon excitation light source 51 (for example, a titanium sapphire pulsed laser) is branched by a beam splitter 91 in two optical paths, so that one pulsed light is incident on a dichroic mirror 53 as stimulation light (pump light) and the other pulsed light is incident on a wavelength conversion element 92 comprising, for example, an optical parametric oscillator, to be converted into erase light having a desired wavelength. The erase light of which wavelength has been converted by the wavelength conversion element 92 is incident on the dichroic mirror 53 via an adjustment lens system 66 and a movable reflecting mirror 67.

Further, it is preferable that a high-dispersion element 93 consisting of, for example, synthetic rutile is placed on an optical path of the erase light between the wavelength conversion element 92 and the dichroic mirror 53 so that the pulse width of the erase light is sufficiently wider than the pulse width of the pump light. FIG. 20 shows a case that the high-dispersion element 93 is placed on the optical path between the adjustment lens system 66 and the movable reflecting mirror 67. Other constitutions and operations are similar to those in the third embodiment as shown in FIG. 5. Accordingly, the two-photon microscope according to the present embodiment comprises an erase light source having a two-photon excitation light source 51 and a wavelength conversion element.

Figure 21:
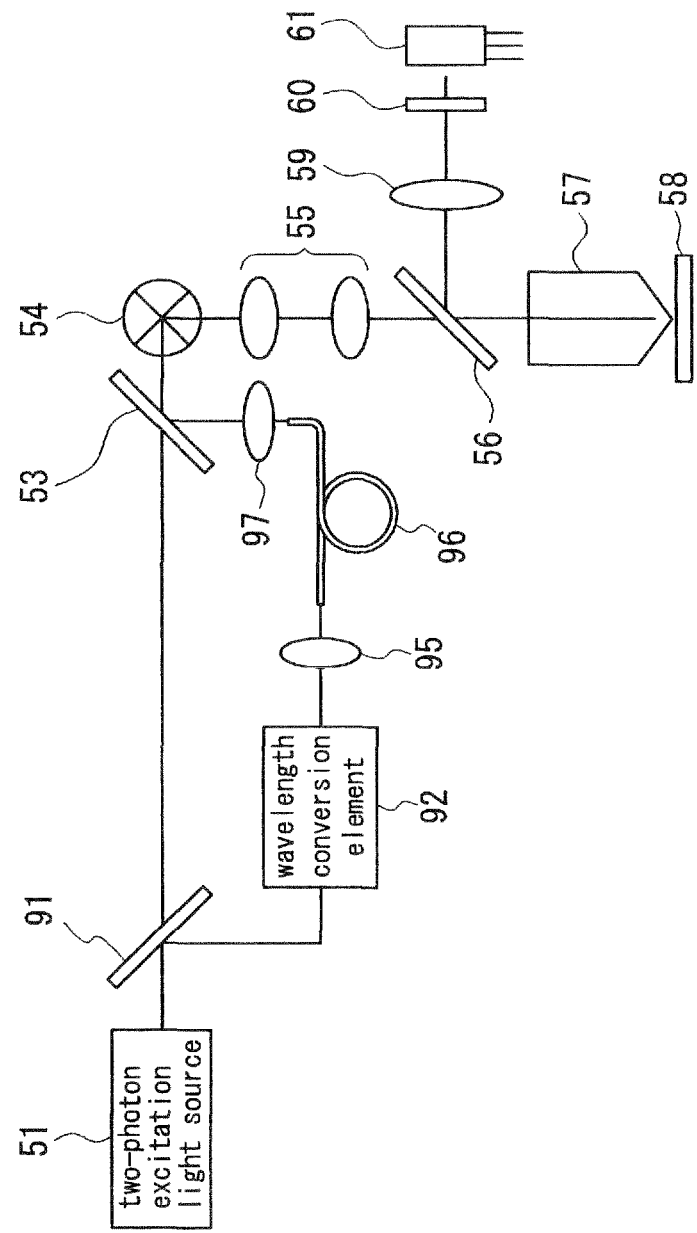
FIG. 21 is a schematic block diagram showing another modified example of the tenth embodiment shown in FIG. 20.

In the present embodiment described above, as in the third embodiment, it is possible to lower a possibility of occurrence of multiphoton excitation due to the erase light by itself and suppress unwanted background light from occurring, so that fluorescence can be detected with a high S/N ratio. As the light dispersion element 93, an optical fiber, a high-dispersion multi-layer film filter, a grating pair, a prism pair may be used other than synthetic rutile. In particular, when an optical fiber is used, for example, as shown in FIG. 21, the erase light from the wavelength conversion element 92 is incident on an optical fiber 96 via a coupling lens 95, and then the erase light output from the optical fiber 96 is incident on the dichroic mirror 53 via a collimating lens 97. Further, the pump light is so adjusted by a beam expander as to have the same beam diameter as that of the erase light incident on the dichroic mirror 53, i.e. to have the same NA. The pump light is then incident on the dichroic mirror 53. Accordingly, use of the optical fiber 96 as a high-dispersion element brings about an advantage that alignment when erase light is introduced is made easier.

Eleventh Embodiment

Figure 22:
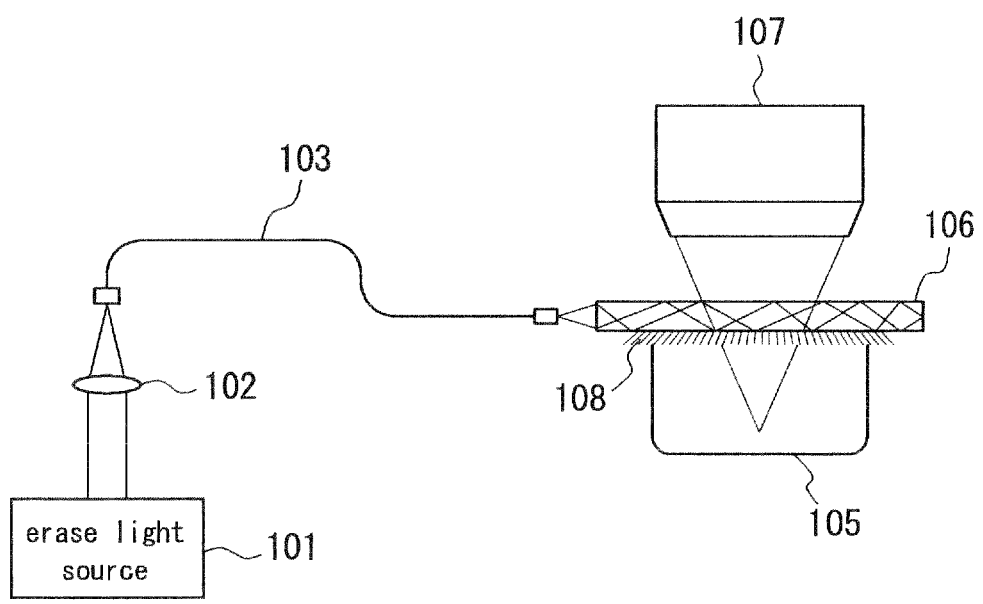
FIG. 22 is a schematic block diagram of a main part of an optical microscope according to an eleventh embodiment of the present invention.

FIG. 22 is a schematic block diagram of a main part of an optical microscope according to an eleventh embodiment of the present invention. The optical microscope according to the present embodiment is substantially the same as the microscope of the foregoing embodiments, except that the former is so configured that evanescent light having two-dimensional sheet-shaped intensity distribution is generated by the erase light, to be irradiated on the sample. Accordingly, in a configuration shown in FIG. 22, the erase light emitted from the erase light source 101 is incident on an optical fiber 103 via a coupling lens 102 and then incident on a side face of a cover glass 106 closely-attached to the surface of the sample 105. Accordingly, the erase light source 101, the coupling lens 102, the optical fiber 103 and the cover glass 106 comprises an erase light irradiation means in this embodiment. Further, the microscope objective lens 107 uses an immersion objective lens or a non-immersion objective lens having a lower refractive index than that of the cover glass 106. The stimulation light is guided to the microscope objective lens 107 in accordance with the microscopes described in the foregoing embodiments.

In FIG. 22, in a case where the sample 105 has a lower refractive index than that of the cover glass 106, the erase light incident from a side face of the cover glass 106 propagates through the cover glass 106 while repeating total reflection at upper and lower interfaces of the cover glass 106. At this time, evanescent light 108 occurs from the interface of the cover glass 106 toward the sample 105 side due to penetration of the erase light. The depth of the evanescent light 108 penetrating through the interface of the cover glass 106, which depends on a total reflection angle in the interface, is generally a few hundred nanometers. Accordingly, the erase light having two-dimensional sheet-like intensity distribution is irradiated on the sample 105.

In this way, by making the evanescent light 108 of the erase light occur at the interface of the cover glass 106 to irradiate the sample 105 therewith, only unnecessary response light in the vicinity of the sample interface can be suppressed and desired response light in the vicinity of the focal point of the pump light is not suppressed at all, whereby detection with a high S/N ratio can be achieved. Although the erase light is made incident on a side face of the cover glass 106 via the optical fiber 103 to generate the evanescent light 108 in the configuration shown in FIG. 22, it is acceptable that the erase light is made incident directly on a side of the cover glass 106 without passing through an optical fiber. Further, it is acceptable to use a super high NA oil-immersion objective lens having NA equal or larger than the refractive index of the sample 105 as the microscope objective lens 107 and make the erase light be incident from the back of the lens at an angle satisfying the total reflection conditions, to generate the evanescent light.

Twelfth Embodiment

Figure 23:
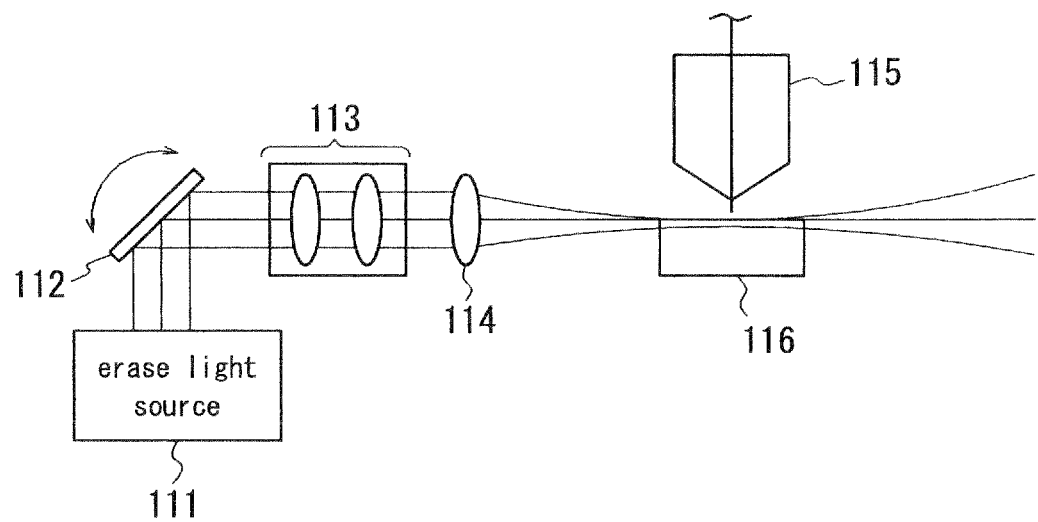
FIG. 23 is a schematic block diagram of a main part of an optical microscope according to a twelfth embodiment of the present invention.
Figure 24:
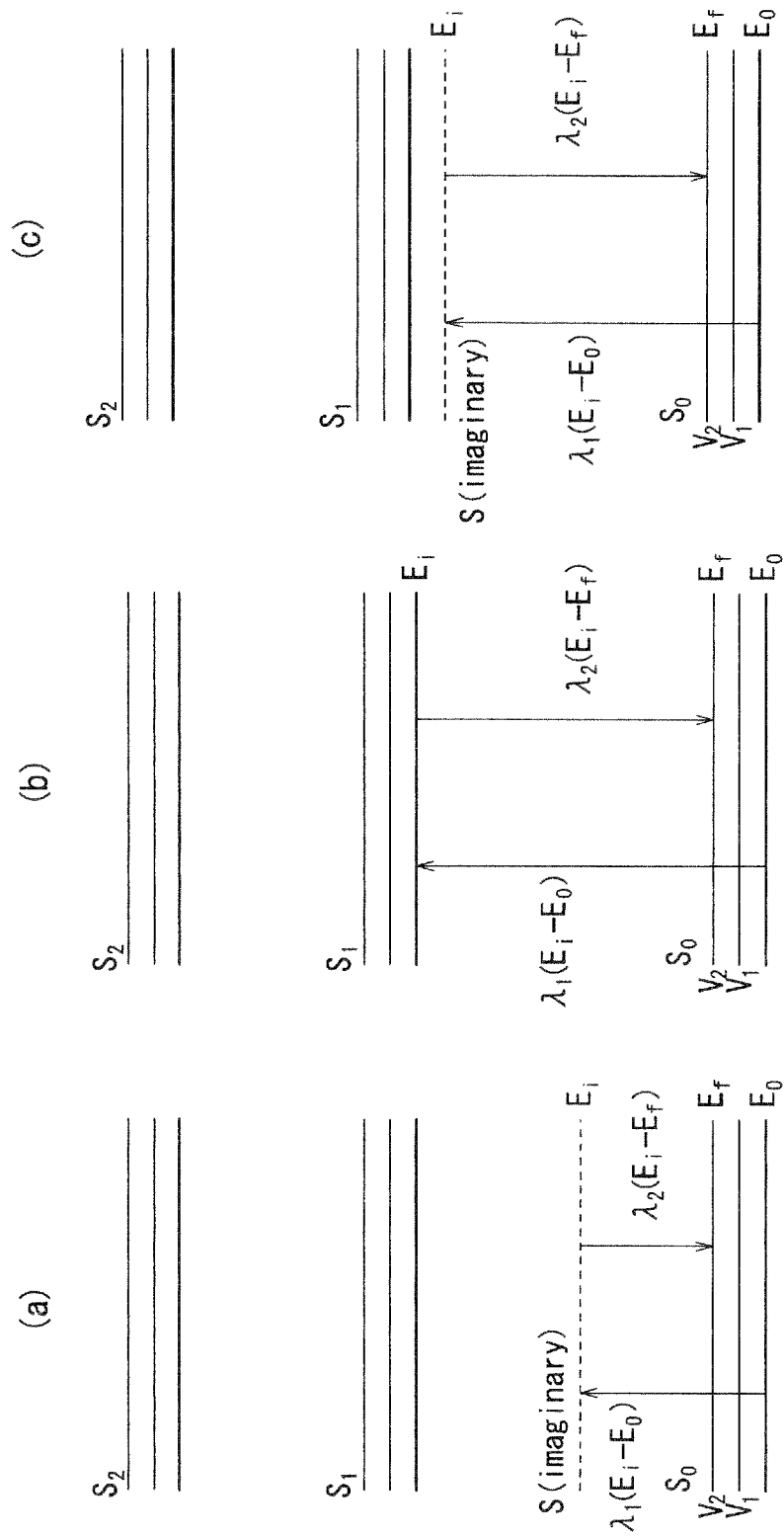
FIG. 24 is an energy diagram explaining non-resonant Raman scattering, true resonance Raman scattering and pre-resonance Raman scattering.
Figure 25:
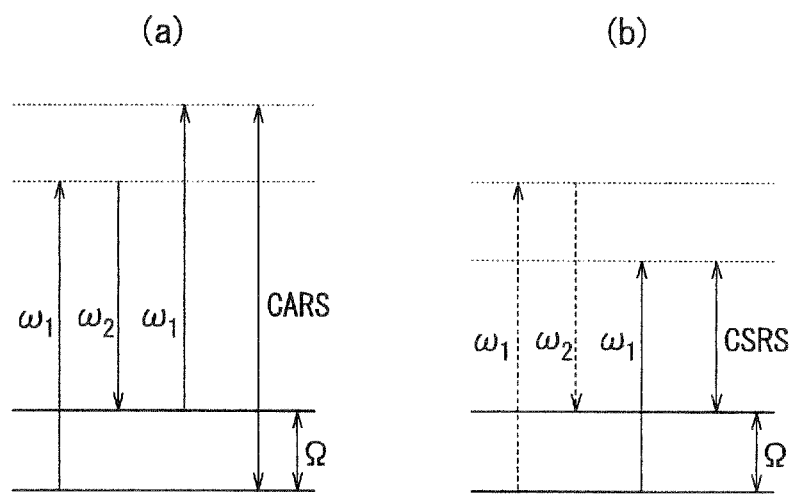
FIG. 25 is an energy diagram explaining coherent Raman scattering.
Figure 26:
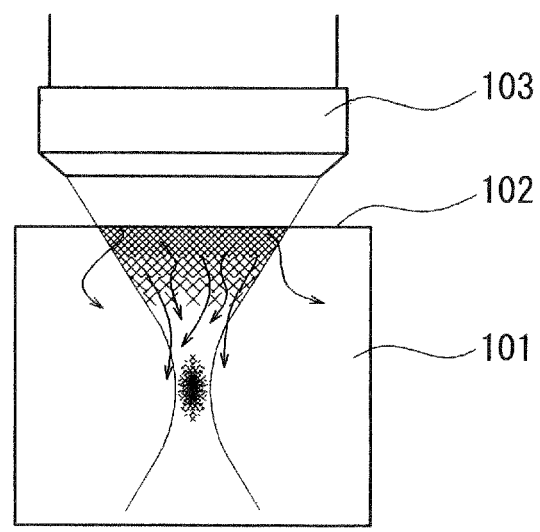
FIG. 26 is a view for explaining the cause of occurrence of background signals in a conventional two-photon microscope.

FIG. 23 is a schematic block diagram of a main part of an optical microscope according to a twelfth embodiment of the present invention. The optical microscope according to the present embodiment is substantially the same as the microscope shown in FIG. 22, except that the former is so configured that the erase light having two-dimensional sheet-shaped intensity distribution is directly irradiated on the sample without generating evanescent light. Due to this, as shown in FIG. 23, the erase light emitted from the erase light source 111 is reflected by an angle variable mirror 112, converted into light having an appropriate beam diameter by a beam expander 113, further converted into illumination light having two-dimensional thin sheet-shaped intensity distribution by a cylindrical lens 114, and the thus-converted light is then irradiated on sample 116 from the direction perpendicular to the observation optical axis of the stimulation light outputted from a microscope objective lens 115. Accordingly, the erase light source 111, the angle variable mirror 112, the beam expander 113, and the cylindrical lens 114 comprises an erase light irradiation means in this embodiment.

According to the arrangement shown in FIG. 23, the depth position of illumination of the sample 116 by the sheet-shaped erase light to can be adjusted by changing an angle of the angle variable mirror 112. Further, the thickness of illumination by the sheet-shaped erase light can be changed by changing the beam diameter of the beam incident on the cylindrical lens 114 by the beam expander 113. In this way, only unnecessary response light at the desired depth of the sample 116 can be suppressed. Therefore, especially in a case where scattering of sample 116 is relatively large and unnecessary response light in the vicinity of the surface is relatively large, only the unnecessary response light can be effectively suppressed.

The present invention is not limited to the aforementioned embodiments but various modifications and changes to the embodiments may be made without departing from the scope of the invention. For example, the erase light used in each of the above-mentioned embodiments for suppressing secondary response light other than the desired response light is not limited to erase light having a single wavelength but may be erase light having a wavelength band. Further, the two-photon excitation light source in the two-photon microscope is not limited to a titanium sapphire pulsed laser of mode lock type but may comprise a semiconductor laser and/or a fiber laser. Since the erase light can reduce a background if only the erase light is irradiated on the sample, it is possible to differentiate the light-collecting position of the stimulation light from that of the erase light by providing an adjusting means of erase light as described in the third embodiment in the optical microscopes described of other embodiments. Further, in recent years, there has been used a technique to observe total reactions of a sample, such as change in form, change in ion density, change in layer potential and the like, by providing a sample with local stimulation in nonlinear optical response process, to analyze functions of a living body. The present invention can also be effectively applied to an optical system for stimulation in such a technique.

What is claimed is:
1. An optical microscope for collecting, on a sample, stimulation light emitted from a stimulation light source and having a single wavelength or a plurality of different wavelengths, and for detecting response light emitted from the sample in a nonlinear optical response process, the microscope comprising:

an erase light source for emitting erase light having a wavelength different from that of the stimulation light and inducing an effect of suppressing secondary response light which appears due to irradiation of the stimulation light on the sample, an optical system configured to simultaneously irradiate the erase light and the stimulation light on the sample such that the erase light does not suppress the response light emitted from a light-collecting area of the stimulation light but suppresses only the secondary response light other than the response light emitted from the light-collecting area of the stimulation light, and an optical element which adjusts a light-collecting position of the erase light and which enables irradiation of the erase light to a position that is three-dimensionally independent from a light-collecting position of the stimulation light such that only the secondary response light is suppressed.

2. The optical microscope according to claim 1, wherein the erase light source emits, as the erase light, light having such a wavelength as to suppress fluorescence of the secondary response light.

3. The optical microscope according to claim 2, further comprising an optical separation element for optically separating the stimulation light and the erase light to be irradiated on the sample from the response light from the sample.

4. The optical microscope according to claim 3, wherein the optical microscope is configured to detect scattered light as the response light.

5. The optical microscope according to claim 4, wherein the optical microscope is configured to detect light which has been stimulated and scattered in a Raman process, as the scattered light.

6. The optical microscope according to claim 5, wherein the optical microscope is configured to detect, as the response light, response light from a sample stained by a fluorescent probe.

7. The optical microscope according to claim 6, wherein the optical microscope is configured to switch between a scattered light detection mode in which the stimulation light and the erase light are simultaneously irradiated on the sample to detect the scattered light and a fluorescence detection mode in which only the stimulation light is irradiated on the sample to detect fluorescence by the fluorescent probe.

8. The optical microscope according to claim 4, wherein the optical microscope is configured to detect light which has been stimulated and scattered in a resonance Raman process, as the scattered light.

9. The optical microscope according to claim 4, wherein the optical microscope is configured to suppress the secondary response light in a double resonance absorption process or a stimulated emission process.

10. The optical microscope according to claim 3, wherein the optical microscope is configured to detect, as the response light, fluorescence induced by a multiphoton absorption process.

11. The optical microscope according to claim 10, wherein the optical microscope is configured to detect, as the response light, fluorescence from a sample stained by a fluorescent probe.

12. The optical microscope according to claim 1, further comprising a wavefront modulation element for modulating a wavefront of the erase light and decreasing peak power at the light-collecting position of the erase light.

13. The optical microscope according to claim 1, wherein the erase light source emits near-infrared light as the erase light.

14. The optical microscope according to claim 1, wherein:
the stimulation light source and the erase light source are pulsed light sources, respectively,
the stimulation light source emits stimulation light having a pulse width of not more than 10 picoseconds, and
the erase light source emits erase light having a pulse width longer than the pulse width of the stimulation light.

15. The optical microscope according to claim 1, wherein the stimulation light source or the erase light source includes one of a titanium sapphire laser, a Nd:YAG laser, a fiber laser, a semiconductor laser and a super-continuum light source.

16. The optical microscope according to claim 1, further comprising:
secondary light detecting means for detecting the secondary response light generated at a surface of the sample; and
an erase light intensity adjusting unit for adjusting an intensity of the erase light emitted from the erase light source based on an output of the secondary light detecting means.

17. The optical microscope according to claim 1, further comprising:
response light detecting means for detecting the response light emitted from the sample;
image processing means for generating an image signal based on an output of the response light detecting means; and
intensity setting means for setting an intensity of the erase light emitted from the erase light source, based on the image signal obtained from the image processing means.

18. The optical microscope according to claim 17, wherein the intensity setting means generates a histogram showing an intensity distribution of the response light, based on the image signal obtained from the image processing means, and sets an optimum intensity of the erase light based on a change in the histogram in relation to intensity change of the erase light emitted from the erase light source.

19. The optical microscope according to claim 1, wherein an intensity of the erase light irradiated on the sample is not more than a predetermined highest intensity under which a second emission phenomenon due to irradiation of the erase light does not occur.

20. The optical microscope according to claim 1, wherein the optical element is placed on an optical path of the erase light, and the optical element includes an adjustment lens which adjusts the light-collecting position and a size of the erase light.

21. The optical microscope according to claim 1, wherein the optical element is placed on an optical path of the erase light, and the optical element includes a movable reflecting mirror which spatially adjusts an optical axis of the erase light independently of the stimulation light.

* * * * *